United States Patent
Kouznetsov et al.

(10) Patent No.: US 8,945,371 B2
(45) Date of Patent: Feb. 3, 2015

(54) DEVICE AND METHODS OF USING A PIEZOELECTRIC MICROBALANCE SENSOR

(71) Applicant: Ecolab USA Inc., Naperville, IL (US)

(72) Inventors: Dmitri L Kouznetsov, Aurora, IL (US); John E Hoots, Batavia, IL (US); Arthur J Kahaian, Chicago, IL (US); Rodney H Banks, Aurora, IL (US); David Ambrose, St. Charles, IL (US)

(73) Assignee: Ecolab USA Inc., Naperville, IL (US)

( * ) Notice: Subject to any disclaimer, the term of this patent is extended or adjusted under 35 U.S.C. 154(b) by 29 days.

(21) Appl. No.: 13/804,440

(22) Filed: Mar. 14, 2013

(65) Prior Publication Data
US 2014/0262202 A1   Sep. 18, 2014

(51) Int. Cl.
*F28F 27/00* (2006.01)
*H01L 41/04* (2006.01)
*G01N 29/24* (2006.01)

(52) U.S. Cl.
CPC ............... *F28F 27/00* (2013.01); *H01L 41/04* (2013.01); *G01N 29/2437* (2013.01)
USPC ......... 205/793.5; 162/198; 162/48; 422/68.1; 422/69; 436/6; 73/64.53; 73/61.62; 73/64.49; 210/745

(58) Field of Classification Search
CPC . G01N 29/2437; G01N 29/2443; F28F 27/00; H01L 41/04
USPC ..................... 204/793.5; 422/68.1, 69; 436/6; 73/64.53, 61.62, 64.49; 162/198, 48; 210/745
See application file for complete search history.

(56) References Cited

U.S. PATENT DOCUMENTS

| | | | |
|---|---|---|---|
| 4,561,286 A | 12/1985 | Sekler et al. | |
| 5,734,098 A | 3/1998 | Kraus et al. | |
| 6,053,032 A | 4/2000 | Kraus et al. | |
| 6,143,800 A | 11/2000 | Nguyen et al. | |
| 6,250,140 B1 | 6/2001 | Kouznetsov et al. | |
| 6,280,635 B1 | 8/2001 | Moriarty et al. | |
| 6,369,894 B1 | 4/2002 | Rasimas et al. | |
| 6,375,829 B1 * | 4/2002 | Shevchenko et al. | 205/793.5 |
| 6,670,617 B2 | 12/2003 | Banks | |
| 6,942,782 B2 * | 9/2005 | Shevchenko et al. | 205/793.5 |
| 7,095,500 B2 | 8/2006 | Banks | |
| 7,154,603 B2 | 12/2006 | Banks | |
| 7,179,384 B2 | 2/2007 | Moriarty et al. | |
| 7,842,165 B2 | 11/2010 | Shevchenko et al. | |
| 8,133,356 B2 * | 3/2012 | Shevchenko et al. | 162/198 |

(Continued)

OTHER PUBLICATIONS

KIPO, International Search Report in International Patent Application No. PCT/US2014/016852, 3 pp., Jun. 11, 2014.

(Continued)

*Primary Examiner* — Jennifer Dieterle
(74) *Attorney, Agent, or Firm* — Leydig, Voit & Mayer, Ltd.

(57) ABSTRACT

Methods for monitoring scale deposition in a water-containing industrial process are disclosed. In certain embodiments, the water-containing industrial process is an aqueous cooling system. In certain embodiments, the methods incorporate fluorometric monitoring and control techniques along with a piezoelectric microbalance sensor. A particular embodiment of a piezoelectric microbalance sensor is additionally disclosed, along with at least one method for using the particular embodiment that is independent of whether fluorometric monitoring and control techniques are utilized.

15 Claims, 12 Drawing Sheets

(56) References Cited

U.S. PATENT DOCUMENTS

2006/0281191 A1 12/2006 Duggirala et al.
2010/0112682 A1 5/2010 Boyette et al.
2011/0266924 A1 11/2011 Spencer, II
2012/0073775 A1 3/2012 Duggirala et al.

OTHER PUBLICATIONS

KIPO, Written Opinion in International Patent Application No. PCT/US2014/016852, 8 pp., Jun. 11, 2014.

* cited by examiner

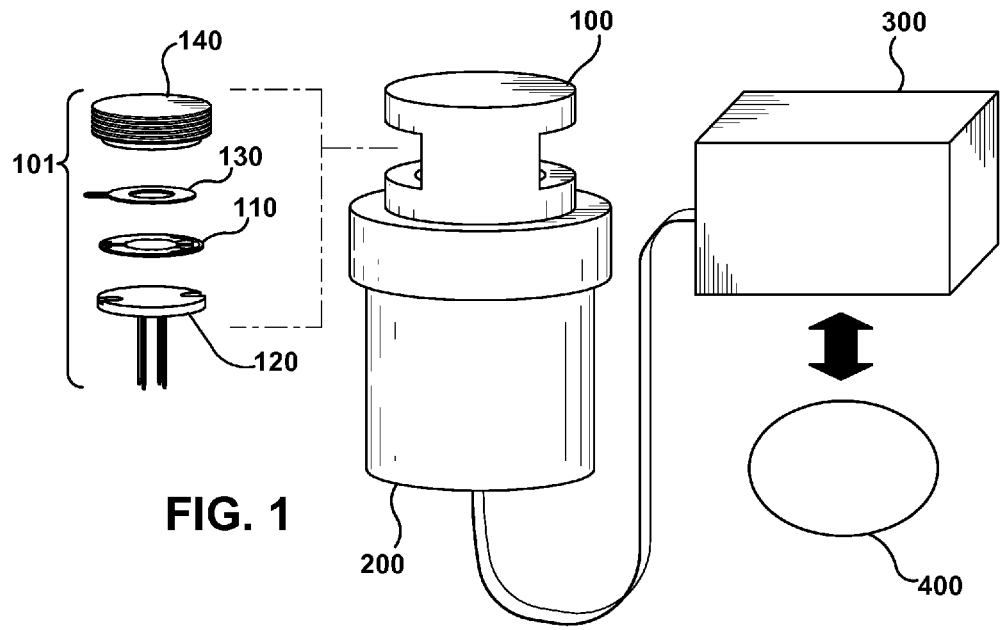
FIG. 1
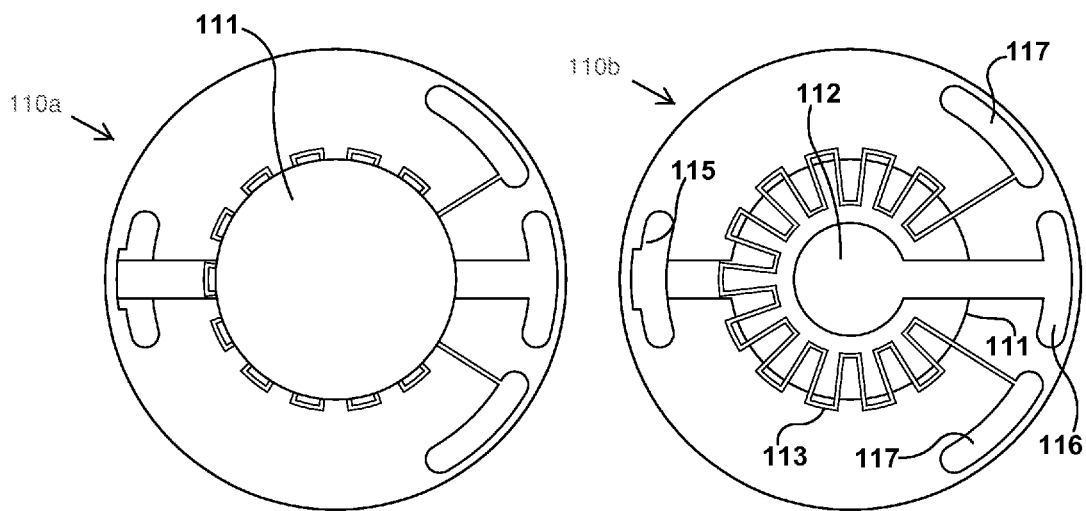
FIG. 2a  FIG. 2b

DEVICE AND METHODS OF USING A PIEZOELECTRIC MICROBALANCE SENSOR

FIELD

The disclosure is directed to the treatment of water-containing industrial processes and measurement of scale or induced scale in water-containing industrial processes.

BACKGROUND

Aqueous cooling systems are subjected to stress during their operation. Many aqueous cooling systems employ a cooling tower that allows heat to dissipate from the cooling water via evaporation. A typical stress to the aqueous cooling system involves mineral scale buildup in the cooling tower, thereby decreasing the efficiency of the cooling tower and aqueous cooling system. Specifically, as the heat in an aqueous cooling system dissipates via evaporation, the components of mineral scale in the remaining water become more concentrated, causing precipitation of the mineral scale on the internals of the cooling tower, and thereby creating operational problems and/or decreased efficiency. Parameters known to typically influence scaling include concentration of scaling species, pH, temperature, flow rate, and concentration of scale-inhibiting chemicals present in the cooling water. Unlike most dissolved species, the solubility of scaling species found in cooling water is typically inversely proportional with temperature (i.e., higher cooling water temperature leads to more scaling). When the aqueous cooling system increases cycles, the concentration of ions such as Ca and Mg increases. To combat this stress the aqueous cooling system is typically blown down and makeup water is added into the system, thereby exchanging a portion of the cooling water for makeup water that is more pure.

Various types of monitoring systems have been used with aqueous cooling systems including those utilizing conductivity meters, and those incorporating fluorometric monitoring and control of treatment chemicals. Piezoelectric microbalance sensors have been utilized in several applications. U.S. Pat. No. 6,250,140 to Kouznetsov et al., the disclosure of which is herein incorporated by reference in its entirety, describes a quartz crystal microbalance device. U.S. Pat. No. 6,143,800 to Nguyen et al.; U.S. Pat. No. 6,375,829 to Shevchenko et al.; U.S. Pat. No. 6,942,782 to Shevchenko et al.; U.S. Pat. No. 7,842,165 to Shevchenko et al.; U.S. Pat. No. 5,734,098 to Kraus et al.; U.S. Patent Application Publication Nos. 2006/0281191 to Duggirala et al. and 2012/0073775 to Duggirala et al. describe quartz crystal microbalance devices and applications.

SUMMARY

In a first exemplary embodiment, the present disclosure is directed to an automated method of monitoring a process upset and recovery of an aqueous cooling system. In a second exemplary embodiment, the present disclosure is directed to an automated method for monitoring dosage and process response of an aqueous cooling system. In a third exemplary embodiment, the present disclosure is directed to an automated method for diagnosing process response to changes in feed water chemistry of a fluorometrically monitored and treated aqueous cooling system.

For each of the first, second, and third exemplary embodiments, the automated method comprises providing an aqueous cooling system comprising cooling water; a fluorometer; a piezoelectric microbalance sensor capable of self-cleaning; and a central control system. The fluorometer and the piezoelectric microbalance sensor are operably connected to the aqueous cooling system and the central control system. At least one water-soluble, scale-inhibiting chemical is dosed at a dosage rate into the cooling water, thereby resulting in a concentration of the at least one water-soluble, scale-inhibiting chemical within the cooling water. The at least one water-soluble, scale-inhibiting chemical is selected from the group consisting of a naturally fluorescing treatment chemical, a fluorescently tagged treatment chemical, a treatment chemical that has been fluorescently traced, and combinations thereof. The concentration of at least one of the at least one water-soluble, scale-inhibiting chemical in the cooling water is fluorometrically measured with the fluorometer. The piezoelectric microbalance sensor is utilized to measure a scaling rate of the cooling water in the aqueous cooling system. At least one process variable of the aqueous cooling system is adjusted in response to at least one of the fluorometric measurement and the measured scaling rate. The at least one process variable is selected from the group consisting of the dosage rate of the at least one water-soluble, scale-inhibiting chemical; a cooling water circulation rate; a valve opening; a flow rate; a volume; a liquid level; pH of the cooling water; blowdown cycle frequency; triggering of an alarm; triggering of a warning; and combinations thereof.

The disclosure may be directed to a fourth exemplary embodiment of a piezoelectric microbalance sensor comprising a piezoelectric material, a heater, a counter-electrode, and a pressure-compensating spacer. The piezoelectric material has a process side suitable for contacting a liquid stream and a non-process side. At least a portion of the process side engages a process side electrode. At least a portion of the non-process side engages a non-process side electrode. The heater is capable of heating the piezoelectric material from the non-process side, thereby enabling temperature control of the piezoelectric material. The counter electrode has a first surface suitable for contacting the liquid stream and facing the process side of the piezoelectric material, and a second opposing surface. The counter-electrode is positioned within the piezoelectric microbalance sensor so as to allow flow of at least a portion of the liquid stream between the process side of the piezoelectric material and the first surface of the counter-electrode. The counter-electrode is constructed of an electrically-conducting, corrosion-resistant material. The pressure-compensating spacer operably contacts the second opposing surface of the counter-electrode. The pressure-compensating spacer is capable of compressing and expanding in response to variations in pressure such as would be created by the liquid stream passing through the piezoelectric microbalance sensor.

The disclosure may also be directed to a fifth exemplary embodiment, which is a method for measuring a scaling rate on a wetted surface within a water-containing industrial process. The method comprises providing a piezoelectric microbalance sensor comprising a piezoelectric material, a heater, a counter-electrode, and a pressure-compensating spacer. The piezoelectric material has a process side suitable for contacting an industrial water stream and a non-process side. At least a portion of the process side engages a process side electrode. At least a portion of the non-process side engages a non-process side electrode. The heater is capable of heating the piezoelectric material from the non-process side, thereby enabling temperature control of the piezoelectric material. The counter-electrode has a first surface suitable for contacting the industrial water stream and facing the process side of the piezoelectric material, and a second opposing surface. The counter-electrode is positioned within the piezoelectric microbalance sensor so as to allow flow of at least a portion of the industrial water stream between the process side of the piezoelectric material and the first surface of the counter-electrode. The counter-electrode is constructed of an electrically-conducting, corrosion-resistant material. The pressure-compensating spacer operably contacts the second opposing surface of the counter-electrode. The pressure-compensating spacer is capable of compressing and expanding in response to variations in pressure such as would be created by the industrial water stream passing through the piezoelectric microbalance sensor. The piezoelectric material is maintained at a constant temperature. While maintaining the piezoelectric material at the constant temperature, the process side of the piezoelectric material and the first surface of the counter-electrode are exposed to the industrial water stream, which contains at least one scaling species capable of precipitation onto the process side of the piezoelectric material. An oscillation frequency of the piezoelectric material is measured for a period of time. Optionally, any change in measured oscillation frequency during the period of time is correlated to a rate of precipitation of the at least one scaling species on the process side of the piezoelectric material. Optionally, at least one process variable of the water-containing industrial process may be adjusted based on the measured oscillation frequency.

BRIEF DESCRIPTION OF THE DRAWINGS

The advantages of the present disclosure will become more readily apparent to those of ordinary skill in the relevant art after reviewing the following detailed description and accompanying drawings, wherein:

FIG. 1 illustrates a view of an embodiment of a piezoelectric microbalance sensor;

FIGS. 2*a* and 2*b* illustrate a view of a process side and a non-process side, respectfully, of an embodiment of the piezoelectric material;

DETAILED DESCRIPTION

Figure 3:
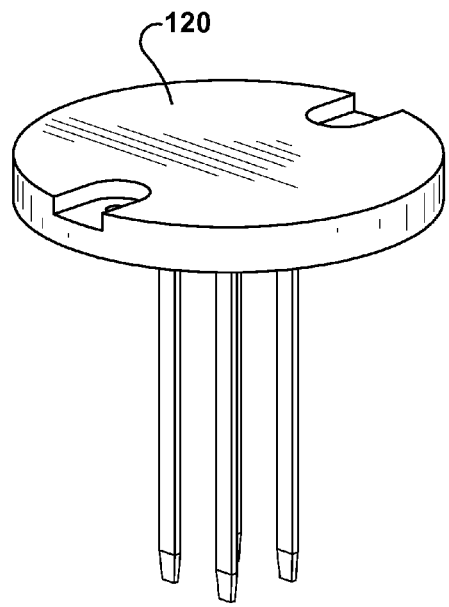
FIG. 3 illustrates an embodiment of a heater that can be used to heat the piezoelectric material from the non-process side.

While embodiments encompassing the general inventive concepts may take various forms, there is shown in the drawings and will hereinafter be described various embodiments with the understanding that the present disclosure is to be considered merely an exemplification and is not intended to be limited to the specific embodiments.

The present disclosure is generally directed to exemplary methods of using fluorometry in combination with at least one piezoelectric microbalance sensor to control an aqueous cooling system and/or treatment thereof.

As it pertains to this disclosure, "piezoelectric" means having the ability to convert mechanical stimulation into a measurable electrical signal. For certain embodiments of the present disclosure, the piezoelectric microbalance sensor is able to convert a detected pressure into a measurable voltage signal.

As it pertains to this disclosure, a "piezoelectric microbalance sensor" is a device that is capable of detecting the presence or absence of mass deposits (e.g., scaling) onto a surface by measured changes in oscillation (a.k.a. vibration) frequency. The fourth exemplary embodiment herein discloses an exemplary embodiment of a piezoelectric microbalance sensor suitable for use in the first, second, or third exemplary embodiments disclosed herein. However, it should be understood that other piezoelectric microbalance sensors (i.e., those different than the fourth exemplary embodiment disclosed herein) can instead be used in certain embodiments of the methods of the first, second, and third embodiments disclosed herein. Generally, a piezoelectric microbalance sensor is capable of measuring scaling and, thereby over time, scaling rate, of cooling water in an aqueous cooling system.

As it pertains to this disclosure, "corrosion-resistant" is used to describe a material that is reasonably able to withstand ordinary chemical conditions associated with the use of the material. For example, a "corrosion-resistant" material under particular chemical conditions may be a particular alloy of stainless steel. As it pertains to this disclosure, the process parts of the piezoelectric microbalance sensor need to be constructed of "corrosion-resistant" materials, particularly the counter-electrode, because of its exposure to potentially extreme chemical conditions (e.g., highly acidic and/or highly basic aqueous liquids).

As it pertains to this disclosure, "pressure-compensating spacer" refers to a component of the piezoelectric microbalance sensor that, when present, allows for another component of the piezoelectric microbalance sensor or a part of another component of the piezoelectric microbalance sensor to somewhat freely move so as to allow for variations in pressure of a liquid that is contacting the apparatus or part. Non-limiting examples of suitable pressure-compensating spacers are described herein, but the present disclosure should not be considered to be limited to those examples.

As it pertains to this disclosure, "taking action" refers to changing a process variable by performing a physical act. Examples of process variables include but are not limited to the following: pump speed, valve position, flow rate (including dosage rate and circulation rate), liquid level, temperature, and pressure. A non-limiting example of "taking action" is described as follows: A process control system determines that a unit operation is too warm and opens a valve in response, thereby allowing cooling water to enter the unit operation. The process control system "took action" by opening the valve.

As it pertains to this disclosure, "sputtering" is a process whereby atoms of metal are deposited on a solid target material due to bombardment of the target material by energetic particles. "Sputtering" allows for metals to be deposited in very thin layers onto substrates.

As it pertains to this disclosure, "trace" refers to a thin deposit around a portion of a substrate. In certain embodiments, a "resistance temperature detector trace" allows for temperature measurement of the substrate via electrical resistance.

As it pertains to this disclosure, "process variable" refers to a measured or calculated value that may be encountered when dealing with an industrial process and/or thermal industrial water process such as an aqueous cooling system. Examples of process variables include but are not limited to the following: temperature; pressure; flow rate (including dosage rate and circulation rate); concentration of one or more chemical species; fluorometric measurements; light or energy absorbance measurements or calculations; ionic measurements/ electrical potential (e.g., electrode measurements, etc.); settling rates/times; flotation rates/times; heat exchange rate; density; turbidity; clarity; scaling potential; titration values; flash point; dew point; volume; mass; statistical calculations; equipment variables (pump speed, valve openings, etc.); process variables (volumes, liquid levels, etc.); blowdown cycle frequency; an alarm or a warning; and so forth.

As it pertains to this disclosure, "self-cleaning" and a "self-cleaning cycle" describe the ability of a piece of equipment to clean itself without or substantially without user intervention. Substantial user intervention implies that a user would need to introduce a cleaning chemical or device other than the piece of equipment itself, or disassemble the piece of equipment or a second directly or indirectly connected piece of equipment in order to physically clean the piece of equipment "by hand." For purposes of this disclosure, a non-limiting example of "without or substantially without user intervention" is the equipment performing a self-cleaning cycle at a user's demand, i.e., when a user directs the self-cleaning cycle to commence instead of the control program automatically instructing commencement of the self-cleaning cycle. Because such cleaning does not require introduction of a cleaning chemical or a device other than the piece of equipment itself, disassembly of the piece of equipment, or a second directly or indirectly connected piece of equipment in order to physically clean the piece of equipment "by hand," performing a self-cleaning cycle at the user's demand is deemed "without or substantially without user intervention."

As it pertains to this disclosure, "operably connected" refers to two or more pieces of equipment that are either directly physically connected, indirectly physically connected, or are able to perform in communication with each other as intended even if not physically connected to each other. For example, a computer may be wirelessly connected to a router that is directly physically connected to a modem that is directly physically connected to the Internet. For this example, the computer is operably connected to the Internet, as are the router and the modem. For this example, the router is indirectly physically connected to the Internet because the router is directly connected to the modem, which is directly connected to the Internet (i.e., the router is physically connected to the Internet via the modem).

As it pertains to this disclosure, "aqueous cooling system" refers to any system that incorporates an aqueous liquid to cool an enclosure or an industrial process. A typical aqueous cooling system will remove heat by utilizing at least one cooling tower or at least one chiller.

As it pertains to this disclosure, a "scale-inhibiting chemical" is a treatment chemical that at a minimum lessens the tendency for scale to form in an aqueous cooling system. Non-limiting examples of scale-inhibiting chemicals include homopolymers, copolymers, terpolymers, and/or tetrapolymers containing one or more of the following monomers: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts, dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, N-vinylpyrrolidone, and combinations thereof.

As it pertains to this disclosure, "quantify" and "quantifying" means measuring and/or calculating an unknown quantity based on at least one measurement of some kind.

As it pertains to this disclosure, "automatic" and "automatically" each mean without or substantially without human intervention. For example, a process carried out automatically would measure a variable and take action (e.g., change a pump speed, increase heating or cooling, etc.) based on the measured variable without a person having to do anything to make the action take place, outside of initially providing any necessary equipment and/or chemical ingredients.

As it pertains to this disclosure, "heat exchanger" refers to any piece of equipment that transfers heat energy from one substance to another. Non-limiting examples of heat exchangers include plate frame, shell and tube, double pipe, cooling tower, chiller, radiator, and coil in tank.

As it pertains to this disclosure, "wetted" refers to a device or component that is contacted by a process liquid (e.g., liquid stream), which in certain embodiments is an aqueous liquid. Additionally, "process side" refers to a side of a device or component that contacts a process liquid (e.g., liquid stream), which in certain embodiments is an aqueous liquid. "Non-process side" refers to the opposing side of the device or component that does not contact a process liquid (e.g., liquid stream), which in certain embodiments is an aqueous liquid.

Related to fluorometric monitoring and control, as it pertains to this disclosure, the term "fluorescent tracing" is used generically to denote "fluorescently monitoring treatment chemicals that are fluorescently traced, fluorescently tagged, or naturally fluorescing," which may be utilized individually or in any combination with one another to fluorometrically monitor and/or control chemical treatment. Unless the context clearly suggests otherwise, the reader should interpret the term "fluorescent tracing" to include any single or combination of the previously listed fluorescence measurement options. Furthermore, fluorescently measuring a fluorescent tracer and correlating the measurement to the concentration of the traced chemical falls within the scope of "fluorometrically measuring" the concentration of the traced chemical.

In a first exemplary embodiment, the present disclosure is directed to an automated method of monitoring a process upset and recovery of an aqueous cooling system. In a second exemplary embodiment, the present disclosure is directed to an automated method for monitoring dosage and process response of an aqueous cooling system. In a third exemplary embodiment, the present disclosure is directed to an automated method for diagnosing process response to changes in feed water chemistry of a fluorometrically monitored and treated aqueous cooling system.

For each of the first, second, and third exemplary embodiments, the automated method comprises providing an aqueous cooling system comprising cooling water; a fluorometer; a piezoelectric microbalance sensor capable of self-cleaning; and a central control system. The fluorometer and the piezoelectric microbalance sensor are operably connected to the aqueous cooling system and the central control system. At least one water-soluble, scale-inhibiting chemical is dosed at a dosage rate into the cooling water, thereby resulting in a concentration of the at least one water-soluble, scale-inhibiting chemical within the cooling water. The at least one water-soluble, scale-inhibiting chemical is selected from the group consisting of a naturally fluorescing treatment chemical, a fluorescently tagged treatment chemical, a treatment chemical that has been fluorescently traced, and combinations thereof. The concentration of at least one of the at least one water-soluble, scale-inhibiting chemical in the cooling water is fluorometrically measured with the fluorometer. The piezoelectric microbalance sensor is utilized to measure a scaling rate of the cooling water in the aqueous cooling system. At least one process variable of the aqueous cooling system is adjusted in response to at least one of the fluorometric measurement and the measured scaling rate. The at least one process variable is selected from the group consisting of the dosage rate at least one water-soluble, scale-inhibiting chemical; a cooling water circulation rate; a valve opening; a flow rate; a volume; a liquid level; pH of the cooling water; blowdown cycle frequency; triggering of an alarm; triggering of a warning; and combinations thereof.

In certain embodiments, the disclosure is directed to a method for monitoring dosage and optionally consumption of treatment chemicals, and a process response of an aqueous cooling system. In certain embodiments, an upset occurs in the aqueous cooling system, and the method monitors the upset and recovery of the aqueous cooling system. In certain embodiments, the upset occurs because of a change in the dissolved chemical species of the makeup water, which over time causes a change in the chemical species of the cooling water.

In certain embodiments, the methods of the present disclosure are implemented in order to inhibit scaling in an aqueous cooling system. In certain embodiments, scaling quantity and/or rate is measured real-time using a piezoelectric microbalance sensor. In certain embodiments, scaling is induced within the piezoelectric microbalance sensor at an elevated temperature, which allows for the prediction of scaling within the aqueous cooling system should the elevated temperature be reached in the aqueous cooling system, particularly in a heat exchanger. In certain embodiments, dosage and consumption of treatment chemicals are also monitored via fluorescent tracing.

In certain embodiments of the first, second, and third exemplary embodiments, the fluorometer comprises a light source and a light emission detector. In certain embodiments, the excitation light source is a solid-state light emitting diode. In certain embodiments, wavelength filters are utilized to isolate a particular wavelength or range of wavelengths. Particular embodiments of suitable fluorometers for use in the discussed methods are described in U.S. Pat. No. 6,369,894, issued Apr. 9, 2002, to Rasimas et al.; U.S. Pat. No. 6,670,617, issued Dec. 30, 2003, to Banks; U.S. Pat. No. 7,095,500, issued Aug. 22, 2006, to Banks; and U.S. Pat. No. 7,154,603, issued Dec. 26, 2006, to Banks; each disclosure of which is herein incorporated by reference in its entirety. Methods of fluorometrically controlling treatment of aqueous cooling systems are described in U.S. Pat. No. 7,179,384 ("the '384 patent"), issued Feb. 20, 2007, to Moriarty et al., the disclosure of which is herein incorporated by reference in its entirety. The '384 patent further describes fluorometric dosing and consumption of at least one treatment chemical using both a fluorescent treatment polymer (either tagged or naturally fluorescing) and a fluorescent tracer.

While a particular embodiment of a piezoelectric microbalance sensor is described in greater detail herein, it is envisioned that the first, second, and third, exemplary embodiments of the methods of the present disclosure may employ a more general piezoelectric microbalance sensor. In certain embodiments, at least one piezoelectric microbalance sensor capable of self-cleaning and at least one fluorometer are operably connected to a central control system that automatically controls a cooling water treatment system based on user input and measurements taken from the at least one piezoelectric microbalance sensor and the at least one fluorometer. In certain embodiments, the central control system comprises a computer as commonly available that is operably programmed to carry out the automated control program. In certain embodiments, the central control system is on site at the site of the aqueous cooling system. In certain embodiments, the central control system is remotely located off site from the aqueous cooling system. In certain embodiments, the central control system is made up of more than one computer. In certain embodiments that employ more than one computer, a portion of the computers is located on site while another portion is located off site. In certain embodiments the central control system comprises a programmable logic control system ("PLC"). The at least one fluorometer and at least one piezoelectric microbalance sensor may be operably connected to the central control system via wireless communication, via wired communication, or via any other known operable communication.

In certain embodiments of the methods, a piezoelectric microbalance sensor is provided. As previously described, piezoelectric microbalance sensors provide the ability to detect pressure caused by the accumulation of scale deposition on the process surface of the piezoelectric material when exposed to cooling water. The scale deposition on the process side can be correlated to scale deposition on a wetted surface of the aqueous cooling system to which the piezoelectric microbalance sensor is deployed via detected oscillation frequency changes in the piezoelectric material. The piezoelectric microbalance sensor converts detected pressure into a measurable and transmittable electrical signal. The detected pressure from the deposited scale creates resonant oscillation in an external driver circuit when energized by alternating current ("A/C"). In certain embodiments, the measurable and transmittable electrical signal is an electrical potential signal (i.e., voltage). In certain embodiments, the piezoelectric microbalance sensor uses a piezoelectric material comprising quartz crystal sandwiched between two conducting electrodes (for the embodiment illustrated herein, the process side electrode 111 and the non-process side electrode 112). The piezoelectric material can be brought to resonant oscillation by the transfer of A/C between the two conducting electrodes. The resonant oscillation is measured, with a decrease in resonant oscillation indicating the deposition of scale onto the process side of the piezoelectric material. In other words, the resonant oscillation should reach a maximum baseline when no deposited mass is present on the process side of the piezoelectric material.

Generally, in certain embodiments of the piezoelectric microbalance sensor, the metals of the process side electrode and non-process side electrode are the same type of metal. In certain embodiments, the metals of the process side electrode and non-process side electrode are two different types of metal. In certain embodiments, the metals are selected from the group consisting of: precious metals, titanium, and combinations thereof. In certain embodiments that incorporate a precious metal, the precious metal is gold. Generally, in certain embodiments, the piezoelectric material of the piezoelectric microbalance sensor oscillates at a reasonably steady frequency unless and until one or more substances become deposited on the piezoelectric material, which thereby causes a corresponding, quantifiable decrease in the frequency depending on the amount of the deposit. The change in frequency is detected and optionally recorded and/or output to a peripheral device such as a monitor, a printer, or similar device.

As previously discussed, scaling typically occurs in aqueous cooling systems because of a combination of several parameters within the cooling water. Non-limiting examples of the several parameters include species concentration, temperature, pH, treatment chemistry, concentration of treatment chemistry, and so forth. A piezoelectric microbalance sensor is capable of directly detecting actual scaling (and/or induced scaling, which is further discussed herein). In other words, the piezoelectric microbalance should detect or predict scaling in the aqueous cooling system regardless of the value of any single parameter.

In certain embodiments, the piezoelectric microbalance sensor provides for real time monitoring of scaling in an aqueous cooling system. In certain embodiments, the piezoelectric microbalance sensor induces scaling thereby allowing for improved dosing of one or more treatment chemicals into the cooling water in order to prevent scaling from occurring in a heat exchanger while substantially not overdosing the cooling water with chemical treatment. In certain embodiments, the piezoelectric microbalance sensor provides a complementary measurement technique to a fluorescence tracing regimen. However, unlike fluorescence, the piezoelectric microbalance sensor will typically be less prone to the presence of elevated turbidity within the aqueous cooling system.

In certain embodiments of the first, second, third, and fifth exemplary embodiments, the piezoelectric material of the piezoelectric microbalance sensor is heated during performance of the methods. As previously discussed, scaling in aqueous cooling systems is generally inversely proportional to temperature, i.e., the chemistry that typically causes scaling becomes less soluble at elevated temperatures. Heating the piezoelectric material provides the ability to induce scaling in the aqueous cooling system, which can provide a significant advantage to the user as a tool to predict scaling before it occurs within the aqueous cooling system.

Arranging to heat the piezoelectric material so that it is warmer than any heat exchanger present in the aqueous cooling system should allow for the minimization of scaling on the heat exchange surfaces because any scaling would first form and be detected on the heated piezoelectric material. Detection of scaling by the piezoelectric microbalance sensor can provide an input for changing of the dosage of at least one water-soluble, scale-inhibiting treatment chemical into the aqueous cooling system. In other words, assuming uniform distribution of adequately dosed water-soluble, scale-inhibiting chemical into the cooling water according to the measurements obtained from a properly deployed piezoelectric microbalance sensor, scaling should never deposit on the corresponding heat exchange surface absent a process upset.

In certain embodiments of the methods of the first, second, third, and fifth exemplary embodiments, the piezoelectric material of a piezoelectric microbalance sensor is heated to be from 1° F. to 75° F. warmer than a heat exchanger within the aqueous cooling system. In certain embodiments, the piezoelectric material of a piezoelectric microbalance sensor is heated to be from 3° F. to 50° F. warmer than a heat exchanger. In certain embodiments, the piezoelectric material of a piezoelectric microbalance sensor is heated from 5° F. to 20° F. warmer than a heat exchanger.

In certain embodiments, the piezoelectric microbalance sensor is capable of self-cleaning. In certain embodiments, the self-cleaning is performed by direct current ("D/C") delivered from the counter-electrode to the process side electrode. The current reversal causes any scaling that may have accumulated on the piezoelectric material to re-dissolve into the liquid contacting the process side of the piezoelectric material.

In certain embodiments, the piezoelectric microbalance sensor is self-cleaned in cycles at regular time intervals. In certain embodiments, the piezoelectric microbalance sensor is self-cleaned in response to at least one frequency measurement made by the piezoelectric microbalance sensor (i.e., the measured scaling rate). In certain embodiments, the self-cleaning is performed on demand. As it relates to the present disclosure, the essence of "self-cleaning" is the ability for the piezoelectric microbalance sensor, in particular the piezoelectric material, to remove scaling deposits from the process side of the piezoelectric material without having to disassemble the piezoelectric microbalance sensor or the aqueous cooling system in any way or taken off line for a substantial period of time.

In certain embodiments, the fluorometer and the piezoelectric microbalance sensor are operably connected to the aqueous cooling system. While theoretically water can be sampled from the at least one aqueous cooling system, placed in a container, and analyzed, the preferred methods of the present disclosure refer to automatically (e.g., on-line and/or real-time) monitoring and optionally controlling treatment of industrial water. In certain embodiments of the present disclosure, an industrial water sample may be removed from the industrial process and discarded after analysis as long as the removal and analysis are performed without or substantially without human intervention.

For purposes of this disclosure, fluorometers may be utilized in any single or a combination of several locations operably attached to the aqueous cooling system. In certain embodiments, the fluorometer is located in a full flow main stream of the aqueous cooling system. In certain embodiments, the fluorescence measurements are taken via a side stream of the aqueous cooling system. In certain embodiments, the fluorometer is located at before and/or after dosing at least one water-soluble, scale-inhibiting chemical selected from the group consisting of: a naturally fluorescing treatment chemical, a fluorescently tagged treatment chemical, and a treatment chemical that has been fluorescently traced. In certain embodiments, the fluorometer is located at a stream attached to a cooling tower basin.

In certain embodiments, the piezoelectric microbalance sensor is located so that the cooling water of an aqueous cooling system (or a stream thereof) contacts the process side of the piezoelectric material and the first surface of the counter-electrode. In certain embodiments, the piezoelectric microbalance sensor is located in a full flow main stream of the aqueous cooling system. In certain embodiments, the piezoelectric microbalance sensor is located at a side stream of the aqueous cooling system. In certain embodiments, the piezoelectric microbalance sensor is located upstream within two feet of a heat exchanger. In certain embodiments, the piezoelectric microbalance sensor is located upstream within six inches of a heat exchanger. In certain embodiments, the piezoelectric microbalance sensor is located downstream within two feet of a heat exchanger. In certain embodiments, the piezoelectric microbalance sensor is located downstream within six inches of a heat exchanger.

In certain embodiments of the methods disclosed herein, at least one water-soluble, scale-inhibiting chemical that is capable of fluorometric quantification is dosed or has been dosed into the aqueous cooling system, thereby resulting in a concentration of the at least one water-soluble, scale-inhibiting chemical within the cooling water. The phrase "capable of fluorometric quantification" is employed to indicate that the at least one water-soluble, scale-inhibiting chemical is either fluorescently traced, fluorescently tagged, or naturally fluorescing. The dosage of the at least one water-soluble, scale-inhibiting treatment chemical beyond any initially utilized dosage is determined by correlating measurements made by at least one of the fluorometer and the piezoelectric microbalance sensor.

In certain embodiments, the concentration of at least one of the at least one water-soluble, scale-inhibiting chemical in the cooling water is fluorometrically measured using at least one fluorometer. The fluorometric measurement allows for quantification of the dosage and optionally measurement of the consumption of the at least one water-soluble, scale-inhibiting treatment chemical. In performing the measurement, excitation light at certain wavelengths is directed into the treated water, and any fluorescent emission at other certain wavelengths is detected using a solid-state detector. The solid-state detector of the fluorometer is responsible for converting the intensity of the fluorescent emission into a quantifiable electrical signal, thereby allowing for the correlation of the fluorescent measurement into a control system input and/or a measured concentration value using a known calibration.

As previously mentioned, the piezoelectric microbalance sensor is capable of measuring scaling within an aqueous cooling system and, thereby over time, scaling rate within an aqueous cooling system. Measurement of dosage of one or more treatment chemicals via fluorescence and scaling rate via a piezoelectric microbalance sensor allows for at least two inputs into the treatment control process, depending on the number of fluorometers and piezoelectric microbalance sensors deployed. Incorporation of a piezoelectric microbalance sensor adds a different type of measurement to the control system, and therefore adds a beneficial level of redundancy.

In certain embodiments, an upset occurs in the aqueous cooling system, and the disclosed methods monitor the upset and recovery of the aqueous cooling system. For example, a process stream may leak into a cooling water stream while treatment dosage of the aqueous cooling system is under control. The process leak may react with the treatment chemical or cause interference with the fluorescence measurement. One or more piezoelectric microbalance sensors can be used in addition to fluorescence monitoring to quickly and accurately monitor the process response to a potentially drastic cooling water quality disruption, which can aid in quickly returning the aqueous cooling system to steady state.

In certain embodiments, the upset occurs because of a change in the dissolved chemical species of the makeup water, which over time causes a change in the chemical species of the cooling water. Such a change in chemical species can be detrimental to the aqueous cooling system, or the change can cause unexpected chemical treatment consumption or false treatment consumption measurements for treatment systems that only monitor chemical dosage and consumption. The combination of fluorometric treatment dosing along with aqueous cooling system response via the piezoelectric microbalance sensor provides a more complete monitoring of the aqueous cooling system than if only one measurement technique is utilized.

In certain embodiments, at least one process variable is adjusted in response to at least one of the fluorometric measurement and the measured rate of scaling. In certain embodiments the at least one process variable is selected from the group consisting of the dosage rate at least one water-soluble, scale-inhibiting chemical; a cooling water circulation rate; a valve opening; a flow rate; a volume; a liquid level; pH of the industrial water (which may be cooling water); blowdown cycle frequency; triggering of an alarm; triggering of a warning; and combinations thereof. For purposes of this disclosure, "blowdown cycling" is a subset of "a valve position."

EXAMPLE

An aqueous cooling system was equipped with a fluorescently monitored dosage and a consumption cooling water treatment system. The fluorescently monitored treatment system indicated that the treatment chemical was being consumed too quickly by the aqueous cooling system, which thereby triggered a substantial increase in dosage of the water-soluble, scale-inhibiting chemical. However, no increase in process temperature within the aqueous cooling system was detected. Because of the substantial increase in dosage that was indicated, the operator stopped the industrial process and aqueous cooling system prior to any equipment failure in order to disassemble and examine the heat exchanger for scaling. The heat exchanger showed no signs of scaling, but the treatment chemical was being consumed at an excessively high rate. Further investigation of the situation provided the answer: An undetected and sharp increase in soluble aluminum concentration had become present in the makeup water. The aluminum was reacting with the treatment chemical causing the drop in fluorescent detection (i.e., the treatment chemical consumption), and thereby triggering the apparent need for an increase in chemical treatment dosage.

To prevent recurrence of this scenario, incorporation of a piezoelectric microbalance sensor into the treatment control system would allow for detection of treatment response (i.e., actual scaling or potential scaling), which could be used to override the apparent need for an increase in fluorescent dosage that was triggered by the fluorometric measurement. The override could slow a metering pump that had initially increased its speed as a result of the fluorescence measurement. The override could also optionally trigger an alarm or warning indicating the occurrence of the discrepancy between the fluorescence measurement and the piezoelectric microbalance sensor measurement.

The disclosure may be directed to a fourth exemplary embodiment of a piezoelectric microbalance sensor comprising a piezoelectric material, a heater, a counter-electrode, and a pressure-compensating spacer. The piezoelectric material has a process side suitable for contacting a liquid stream and a non-process side. At least a portion of the process side engages a process side electrode. At least a portion of the non-process side engages a non-process side electrode. The heater is capable of heating the piezoelectric material from the non-process side, thereby enabling temperature control of the piezoelectric material. The counter electrode has a first surface suitable for contacting the liquid stream and facing the process side of the piezoelectric material, and a second opposing surface. The counter-electrode is positioned within the piezoelectric microbalance sensor so as to allow flow of at least a portion of the liquid stream between the process side of the piezoelectric material and the first surface of the counter-electrode. The counter-electrode is constructed of an electrically-conducting, corrosion-resistant material. The pressure-compensating spacer operably contacts the second opposing surface of the counter-electrode. The pressure-compensating spacer is capable of compressing and expanding in response to variations in pressure such as would be created by the liquid stream passing through the piezoelectric microbalance sensor.

The disclosure may also be directed to a fifth exemplary embodiment, which is a method for measuring a scaling rate on a wetted surface within a water-containing industrial process. The method comprises providing a piezoelectric microbalance sensor comprising a piezoelectric material, a heater, a counter-electrode, and a pressure-compensating spacer. The piezoelectric material has a process side suitable for contacting an industrial water stream and a non-process side. At least a portion of the process side engages a process side electrode. At least a portion of the non-process side engages a non-process side electrode. The heater is capable of heating the piezoelectric material from the non-process side, thereby enabling temperature control of the piezoelectric material. The counter electrode has a first surface suitable for contacting the industrial water stream and facing the process side of the piezoelectric material, and a second opposing surface. The counter-electrode is positioned within the piezoelectric microbalance sensor so as to allow flow of at least a portion of the industrial water stream between the process side of the piezoelectric material and the first surface of the counter-electrode. The counter-electrode is constructed of an electrically-conducting, corrosion-resistant material. The pressure-compensating spacer operably contacts the second opposing surface of the counter-electrode. The pressure-compensating spacer is capable of compressing and expanding in response to variations in pressure such as would be created by the industrial water stream passing through the piezoelectric microbalance sensor. The piezoelectric material is maintained at a constant temperature. While maintaining the piezoelectric material at the constant temperature, the process side of the piezoelectric material and the first surface of the counter-electrode are exposed to the industrial water stream, which contains at least one scaling species capable of precipitation onto the process side of the piezoelectric material. An oscillation frequency of the piezoelectric material is measured for a period of time. Optionally, any change in measured oscillation frequency during the period of time is correlated to a rate of precipitation of the at least one scaling species on the process side of the piezoelectric material. Optionally, at least one process variable of the water-containing industrial process may be adjusted based on the measured oscillation frequency.

While the aforementioned methods according to the first, second, and third embodiments disclosed herein may be practiced with a piezoelectric microbalance sensor other than the one described below, the aforementioned methods may also be practiced using the piezoelectric microbalance sensor described in greater detail below.

Regarding the figures, FIG. 1 illustrates a view of an embodiment of a piezoelectric microbalance sensor 101 that is operably connected to a central control unit 400 (operable connection indicated by the two-way arrow). FIG. 1 includes an exploded view of the piezoelectric microbalance sensor 101. For the illustrated embodiment, the piezoelectric microbalance sensor 101 is mounted inside a sensor housing 100 that is able to provide open space so that liquid may flow in the channel between the piezoelectric material 110 and the counter-electrode 130. The sensor housing 100 is operably attached to a driver 200, which is responsible for supplying a quantifiable electrical current to the piezoelectric material and translating the oscillation frequency of the piezoelectric material to a variable voltage signal. For the illustrated embodiment, the driver 200 is operably connected to a support module 300, which is operably connected to a central control unit 400. In certain embodiments, the support module 300 may be built as part of the driver 200 or as part of the central control unit 400.

Turning to FIG. 2, FIGS. 2a and 2b illustrate a view of a process side 110a and a non-process side 110b, respectfully, of an embodiment of the piezoelectric material 110. FIG. 2a illustrates an embodiment of the process side 110a engaging a process side electrode 111, the process side electrode being deposited onto the process side 110a of the piezoelectric material 110. The process side 110a, in operation, contacts the liquid stream. In certain embodiments, the process side electrode 111 is constructed of a precious metal. In certain embodiments, the precious metal is gold.

FIG. 2b illustrates a view of the non-process side 110b of an embodiment of the piezoelectric material 110. FIG. 2b shows the non-liquid-contacting side (i.e., reverse side) of the process side electrode 111, which for purposes of illustration can be seen through the piezoelectric material 110 and is operably attached to the driver 200 via wraparound contact 115. A non-process side electrode 112 has been deposited onto the non-process side 110b of the piezoelectric material 110. The non-process side electrode 112 is operably connected to the driver 200 via contact 116. In certain embodiments, the metals of the process side electrode 111 and the non-process side electrode 112 are the same type of metal. In certain embodiments, the metals of the process side electrode 111 and the non-process side electrode 112 are two different types of metals. In certain embodiments, the metals of the process side electrode 111 and the non-process side electrode 112 are each independently selected from the group consisting of: precious metals, titanium, and combinations thereof. In certain embodiments that incorporate a precious metal, the precious metal is gold.

In certain embodiments, a resistance temperature detector ("RTD") trace 113 is deposited onto the non-process side 110b of the piezoelectric material 110. Incorporation of the optional RTD trace 113 allows for direct measurement of the temperature of the piezoelectric material 110. In certain embodiments, RTD trace 113 comprises a square wave serpentine pattern that surrounds at least a portion of the non-process side electrode 112. In the illustrated embodiment, the RTD trace 113 consists of titanium and platinum, where titanium serves as a thin adhesion layer to the quartz piezoelectric material 110, and platinum is thicker than the thin adhesion layer and serves as the RTD sensor. For the illustrated embodiment, the RTD trace 113 is operably connected to the driver 200 via two contacts 117.

Turning to FIG. 3, FIG. 3 illustrates an embodiment of a heater 120 capable of heating the piezoelectric material 110 from the non-process side 110b, which thereby enables temperature control of the piezoelectric material 110. In certain embodiments, the heater 120 is a resistance heater. In certain embodiments, the heater 120 is constructed of a corrosion-resistant material. In certain embodiments, the corrosion-resistant material is ceramic. In certain embodiments, the heater 120 is operably connected throughout the cross-section of the piezoelectric material 110.

Figure 4:
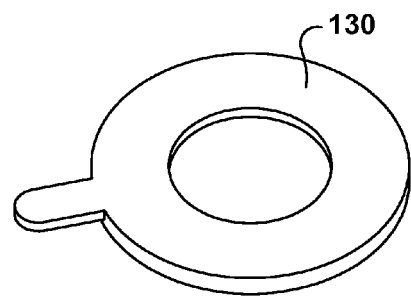
FIG. 4 illustrates an embodiment of a counter-electrode.

Turning to FIG. 4, FIG. 4 illustrates an embodiment of a counter-electrode 130, which has a first surface suitable for contacting the liquid stream and facing the process side 110a of the piezoelectric material 110, and a second opposing surface. In certain embodiments, the counter-electrode is positioned within the piezoelectric microbalance sensor 101 so as to allow flow of at least a portion of the liquid stream between the process side 110a of the piezoelectric material 110 and the first surface of the counter-electrode 130. For the illustrated embodiment, the counter-electrode 130 comprises an optional void in its center, thereby allowing liquid to contact the pressure-compensating spacer 140 of the illustrated embodiment. In certain embodiments, the counter-electrode 130 is constructed of an electrically-conducting, corrosion resistant material.

Figure 5:
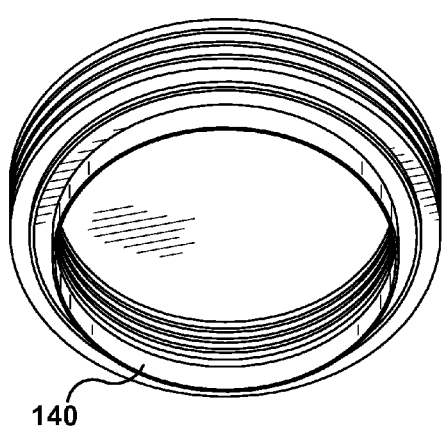
FIG. 5 illustrates an embodiment of a pressure-compensating spacer.

Turning to FIG. 5, FIG. 5 illustrates an embodiment of a pressure-compensating spacer 140, which for the illustrated embodiment takes the form of a bellows. For certain embodiments, at least one O-ring (not shown), at least one gasket (not shown), and/or at least one diaphragm (not shown) take the place of or are used in combination with a bellows and/or each other.

Figure 6:
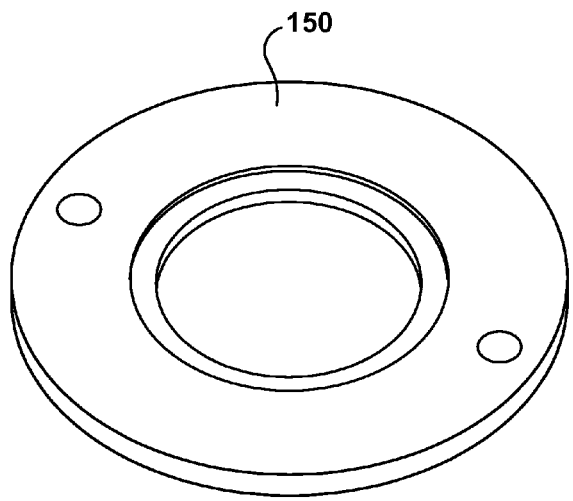
FIG. 6 illustrates an embodiment of a brace that may be employed to attach and support the counter-electrode and the pressure-compensating spacer.

Turning to FIG. 6, FIG. 6 illustrates an embodiment of a brace 150 (not illustrated in FIG. 1) that may be employed to mount the counter-electrode 130 to the pressure-compensating spacer 140. Depending on the specific embodiment of the counter-electrode and pressure-compensating spacer, a brace or support member may be necessary to mount the counter-electrode to the pressure-compensating spacer. For the illustrated embodiment, the purpose of the brace 150 is to provide support for the counter-electrode 130 and to provide channels so that oil (not shown) can enter and leave the illustrated bellows as necessary. In certain embodiments, oil is utilized within the bellows to allow for mechanical pressure compensation in the form of compression and expansion in response to variable liquid pressure in the channel between the piezoelectric material 110 and the counter-electrode 130.

In certain embodiments, the piezoelectric microbalance sensor comprises a counter-electrode having a first surface suitable for contacting the liquid stream and facing the process side of the piezoelectric material, and a second opposing surface. The counter-electrode is positioned within the piezoelectric microbalance sensor so as to allow flow of at least a portion of the liquid stream from a water-containing industrial process between the process side of the piezoelectric material and the first surface of the counter-electrode. In certain embodiments, the counter-electrode is constructed of an electrically-conducting, corrosion-resistant material. In certain embodiments, the electrically-conducting, corrosion-resistant material is a stainless steel. In certain embodiments, the electrically-conducting, corrosion-resistant material is a Hastelloy steel. In certain embodiments, the electrically-conducting, corrosion-resistant material is graphite.

As previously discussed, a piezoelectric microbalance sensor detects pressure and converts the detected pressure into measurable voltage. The detected pressure creates resonant oscillation in a driver circuit when energized by A/C. The resonant oscillation can be measured as change in voltage. In certain embodiments, the piezoelectric microbalance sensor utilizes a piezoelectric material comprising quartz crystal. In certain embodiments, the process side electrode comprises gold. In certain embodiments, the non-process side electrode comprises gold. The piezoelectric material can be brought to resonant oscillation by the transfer of A/C between the process side electrode and the non-process side electrode. The electrical signal that corresponds to the resonant oscillation is measured, with a decrease in voltage indicating a decrease in resonant oscillation, which indicates that scale has deposited onto the process side of the piezoelectric material. In other words, the resonant oscillation should reach a maximum baseline when no deposited mass is present on the process side of the piezoelectric material.

In certain embodiments, the piezoelectric microbalance sensor has a pressure-compensating spacer that operably contacts the second opposing surface of the counter-electrode. When utilized, the pressure-compensating spacer compresses and expands as necessary to compensate for variable liquid pressure in the liquid stream passing through the piezoelectric microbalance sensor. In certain embodiments, the pressure-compensating spacer is selected from the group consisting of at least one bellows, at least one diaphragm, at least one O-ring, at least one gasket, and combinations thereof. In certain embodiments, the pressure-compensating spacer takes the form of a bellows. In certain embodiments, the pressure-compensating spacer takes the form of at least one O-ring. In certain embodiments, the pressure-compensating spacer takes the form of at least one gasket. In certain embodiments, the pressure-compensating spacer employs a combination of at least two of the following: a bellows, an O-ring, and a gasket.

Figure 7A:
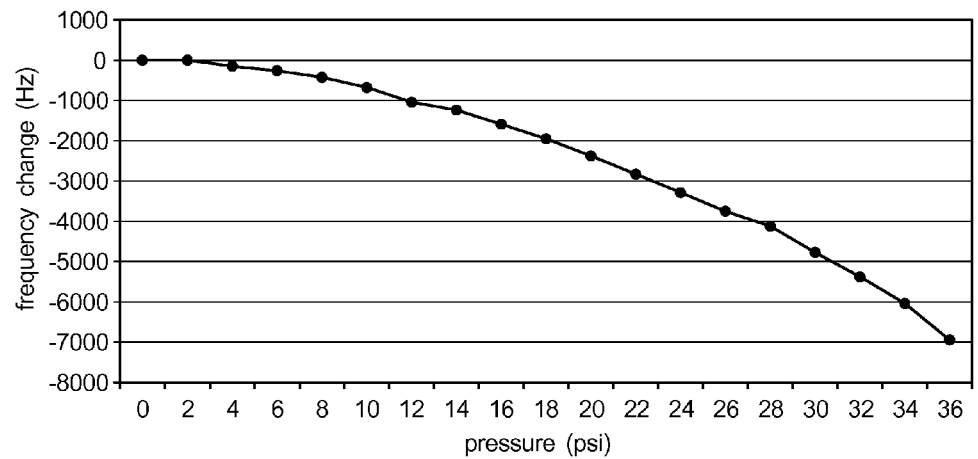
FIGS. 7*a* and 7*b* graphically contrast the effects of variable liquid pressure on frequency measurements generated with and without pressure compensation.
Figure 7B:
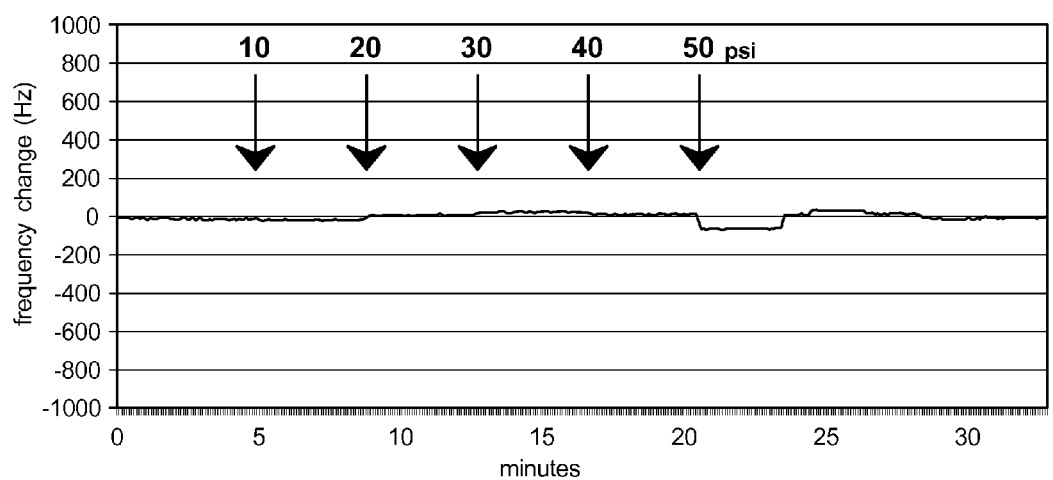

Turning to FIG. 7, the graphs illustrated in FIGS. 7a and 7b contrast the effects of variable liquid pressure on frequency measurements generated with and without pressure compensation. FIG. 7(b) illustrates that mechanical pressure compensation can allow for reasonably consistent scaling deposition measurement using a piezoelectric microbalance sensor. FIG. 7(a) illustrates that, without pressure compensation, variation in liquid pressure can cause error in the measurement.

While circular and somewhat flattened (i.e., "coin-shaped") embodiments of the several elements of the piezoelectric microbalance sensor have been illustrated, it should be understood that various elements may take any of several other physical forms. In certain embodiments, the piezoelectric material is a quartz crystal with at least two metal electrodes deposited onto opposing surfaces. In certain embodiments, the quartz crystal is sputtered with at least one titanium electrode. In certain embodiments, the quartz crystal is sputtered with at least one gold electrode. In certain embodiments, the piezoelectric material is a quartz crystal that has a central portion of one side sputtered with a gold electrode and a second portion of an opposing side sputtered with a gold or titanium electrode.

In certain embodiments, an RTD trace is configured around the piezoelectric material thereby allowing for direct temperature measurement of the piezoelectric material. In certain embodiments that utilize an RTD trace, the RTD trace comprises platinum. In certain embodiments utilizing the RTD trace, the RTD trace can have a square wave serpentine pattern overlapping the second portion.

In certain embodiments, the piezoelectric microbalance sensor is constructed to allow for temperature variations ranging from about 32° F. to about 160° F. In certain embodiments, the piezoelectric microbalance sensor is constructed so as to compensate for pressure of the liquid stream up to 100 psig.

In certain embodiments, a heater is utilized that is capable of heating the piezoelectric material from the non-process side and thereby enables temperature control of the piezoelectric material. Any electrical resistance heater is contemplated as long as the heater meets any size requirements (i.e., is small), is capable of heating the entire piezoelectric material in a reasonably uniform manner, and is capable of maintaining a constant temperature (i.e., ±2° F.) when so controlled. In certain embodiments, the heater is a resistance heater. In certain embodiments, the heater is directly connected to the piezoelectric material. In certain embodiments, the heater is operably connected throughout the cross-section of the piezoelectric material. In certain embodiments, the heater is a ceramic heater.

In certain embodiments, the setpoint of the temperature of the piezoelectric material is variable and can be set as needed depending on the particular aqueous cooling system. In certain embodiments, the piezoelectric material is maintained at a constant temperature (i.e., not more than ±3° F. from a setpoint). For such embodiments, the piezoelectric material should be heated to and maintained at an elevated setpoint to simulate stress at a particular heat exchanger, which ideally will be located in relatively close proximity to the piezoelectric microbalance sensor.

In certain embodiments, the piezoelectric microbalance sensor comprises several interchangeable parts. In other words, such embodiments can be disassembled and reassembled. Such embodiments may, from time to time, incorporate replacement parts in place of the originally-assembled parts.

In certain embodiments, the piezoelectric microbalance sensor is operably attached to an automated industrial water treatment system. In certain embodiments, the automated industrial water treatment system treats cooling water used in an aqueous cooling system. In certain embodiments, the automated industrial water treatment system treats the cooling water to inhibit scale formation.

In certain embodiments, the piezoelectric microbalance sensor is self-cleaning. In certain embodiments, the piezoelectric microbalance sensor is in communication with a controller that is programmed with an automated piezoelectric microbalance sensor self-cleaning cycle. In certain embodiments, the self-cleaning cycle can be activated "on demand," i.e., at the user's discretion. In certain embodiments, the automated piezoelectric microbalance sensor self-cleaning cycle is programmed to operate the self-cleaning cycle at one or more particular time intervals. In certain embodiments, the automated piezoelectric microbalance sensor self-cleaning cycle is programmed to operate the self-cleaning cycle at the occurrence of one or more particular measurement events. Examples of such measurement events may include a statistical "out-of-control" event, achieving a particular scaling measurement, and so forth.

Figure 8:
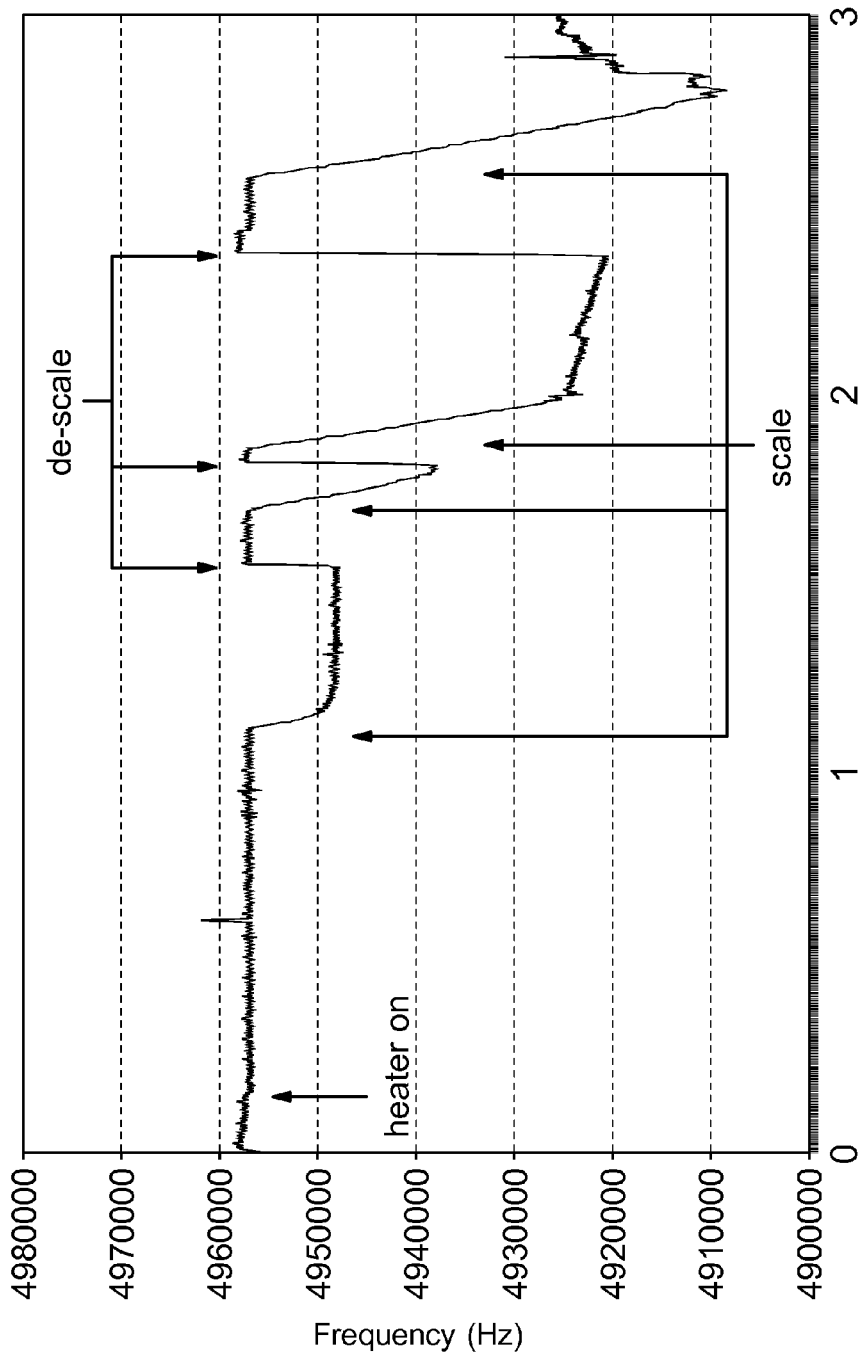
FIG. 8 graphically illustrates several de-scaling self-cleaning cycles of an embodiment of a piezoelectric microbalance sensor.

A self-cleaning piezoelectric microbalance sensor has the advantage of being able to clean the process side of the piezoelectric material without user intervention (e.g., shutting down the aqueous cooling system and/or removing the piezoelectric microbalance sensor or a portion thereof from the aqueous cooling system). While cathodic polarization can induce scaling on the process side of the piezoelectric material, anodic polarization reverses the effects and removes the induced scaling that is dissolved at acidic pH. By employing anodic polarization at the process side electrode, the process side of the piezoelectric material can be quickly cleaned and returned into reliable service without major user intervention. The cleaning cycle hydrolyzes water, creating acidic conditions at the process side electrode and creating oxygen as an off gas. FIG. 8 graphically illustrates the execution of several self-cleaning cycles of an embodiment of the piezoelectric microbalance sensor 101.

Figure 9:
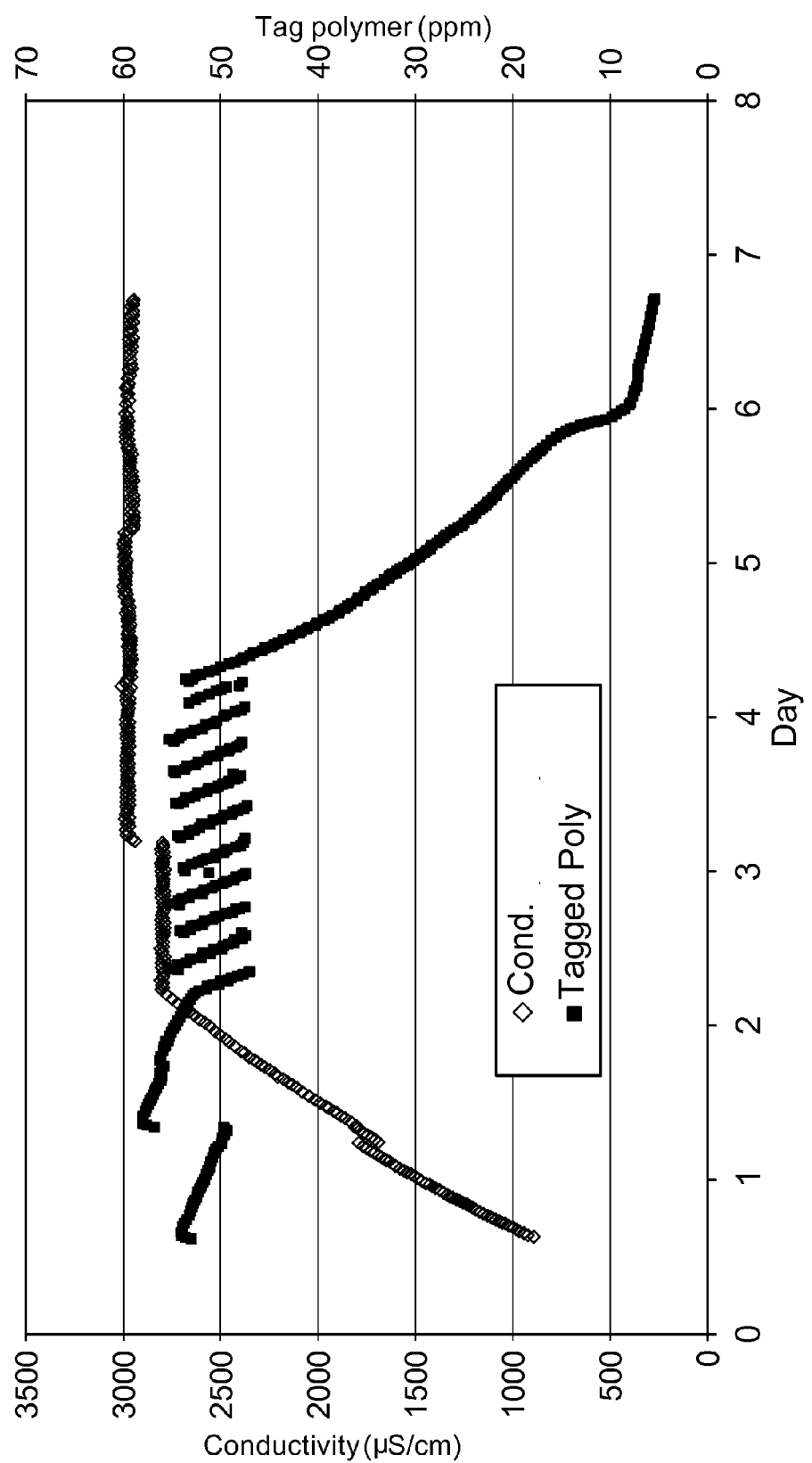
FIG. 9 graphically illustrates for comparative purposes the response of a conductivity sensor when scale-inhibiting chemical treatment dosage is interrupted.

Turning to FIG. 9, the graph of FIG. 9 illustrates for comparative purposes the response of a conductivity sensor and fluorometric measurement of a fluorescently tagged scale-inhibiting treatment chemical (polymer) when the scale-inhibiting treatment chemical dosage is interrupted. The dosage was stopped around Day 4. The fluorometric measurement observed the stoppage, but the conductivity meter had not detected any stoppage as of Day 7.

Figure 10:
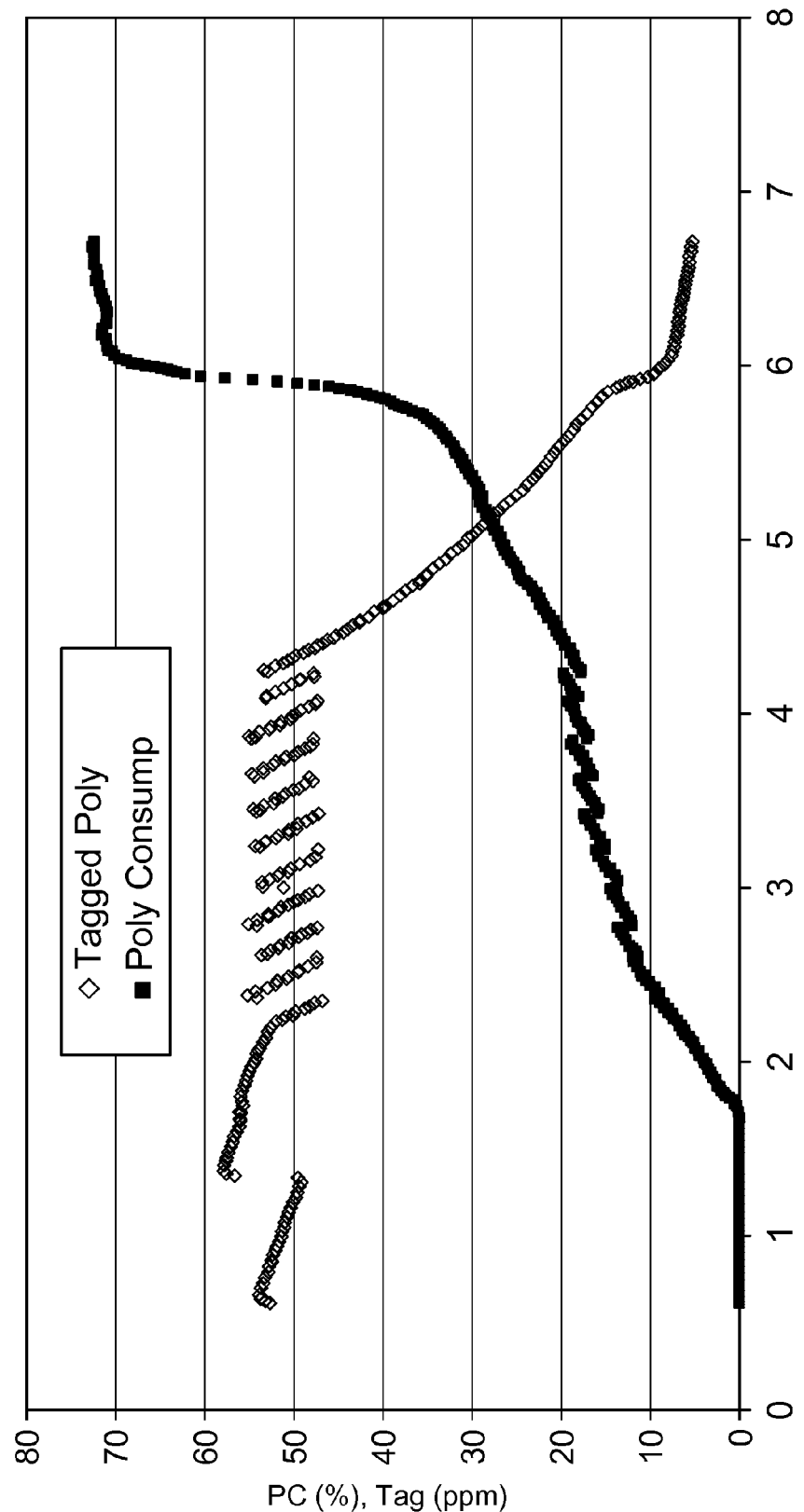
FIG. 10 graphically illustrates scale-inhibiting treatment chemical (i.e., polymer) consumption for the same experiment illustrated in FIG. 9.

Turning to FIG. 10, the graph of FIG. 10 plots scale-inhibiting treatment polymer consumption along with the fluorescently tagged polymer concentration for the same experiment illustrated in FIG. 9. When dosage was stopped around Day 4, treatment polymer consumption began to increase, with a sharp rise shown toward the end of Day 6.

Figure 11:
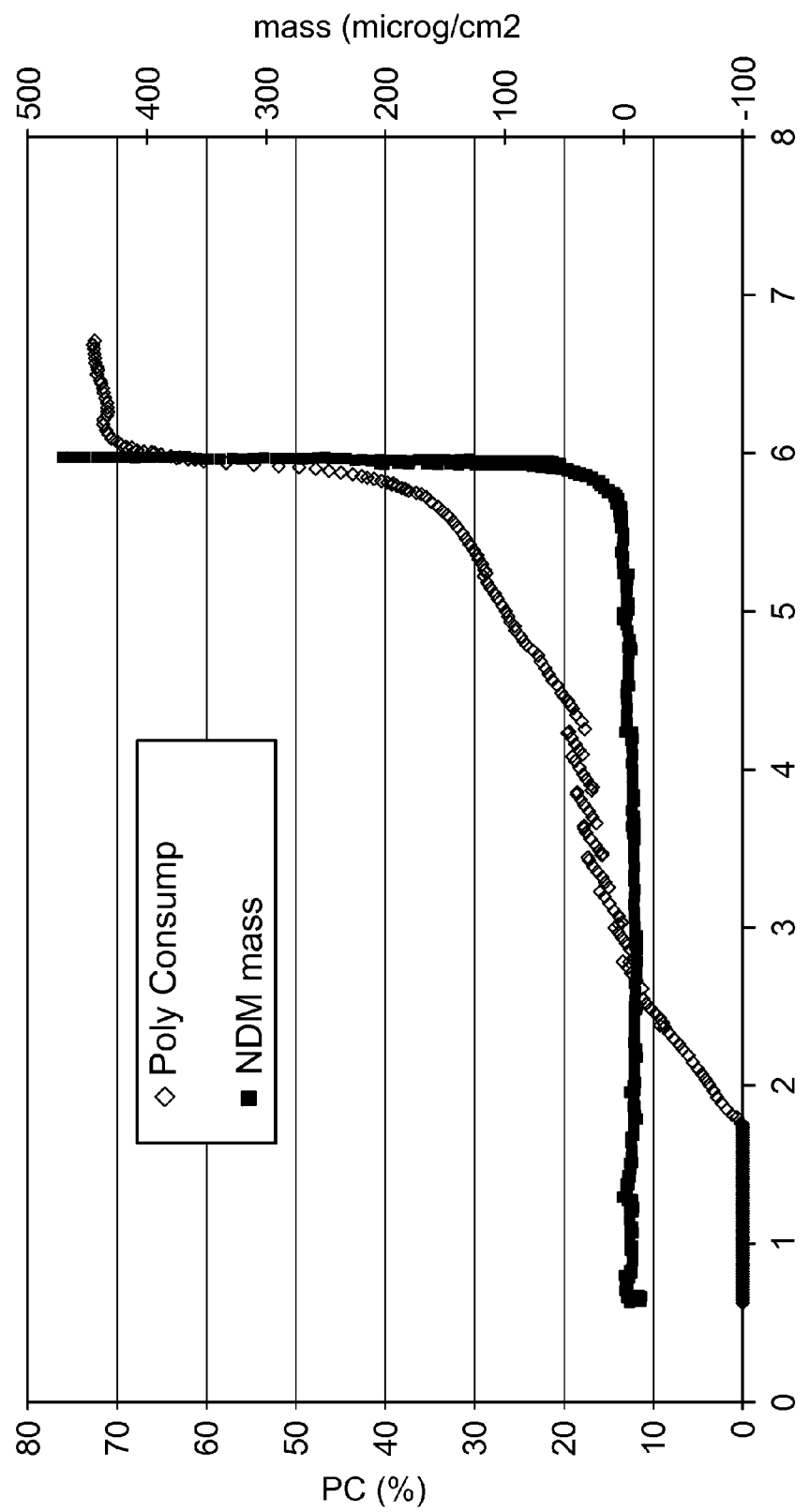
FIG. 11 graphically illustrates the scaling response as measured by a piezoelectric microbalance sensor (marked as "NDM mass") for the same experiment illustrated in FIGS. 9 and 10.

Turning to FIG. 11, the graph of FIG. 11 illustrates the polymer consumption and the scaling response as measured by a piezoelectric microbalance sensor (marked as "NDM mass") for the same experiment illustrated in FIGS. 9 and 10. Unlike the conductivity measurement illustrated in FIG. 9, the piezoelectric microbalance sensor was able to detect the scaling event caused by the spike in scale-inhibiting treatment polymer consumption shown toward the end of Day 6.

Figure 12:
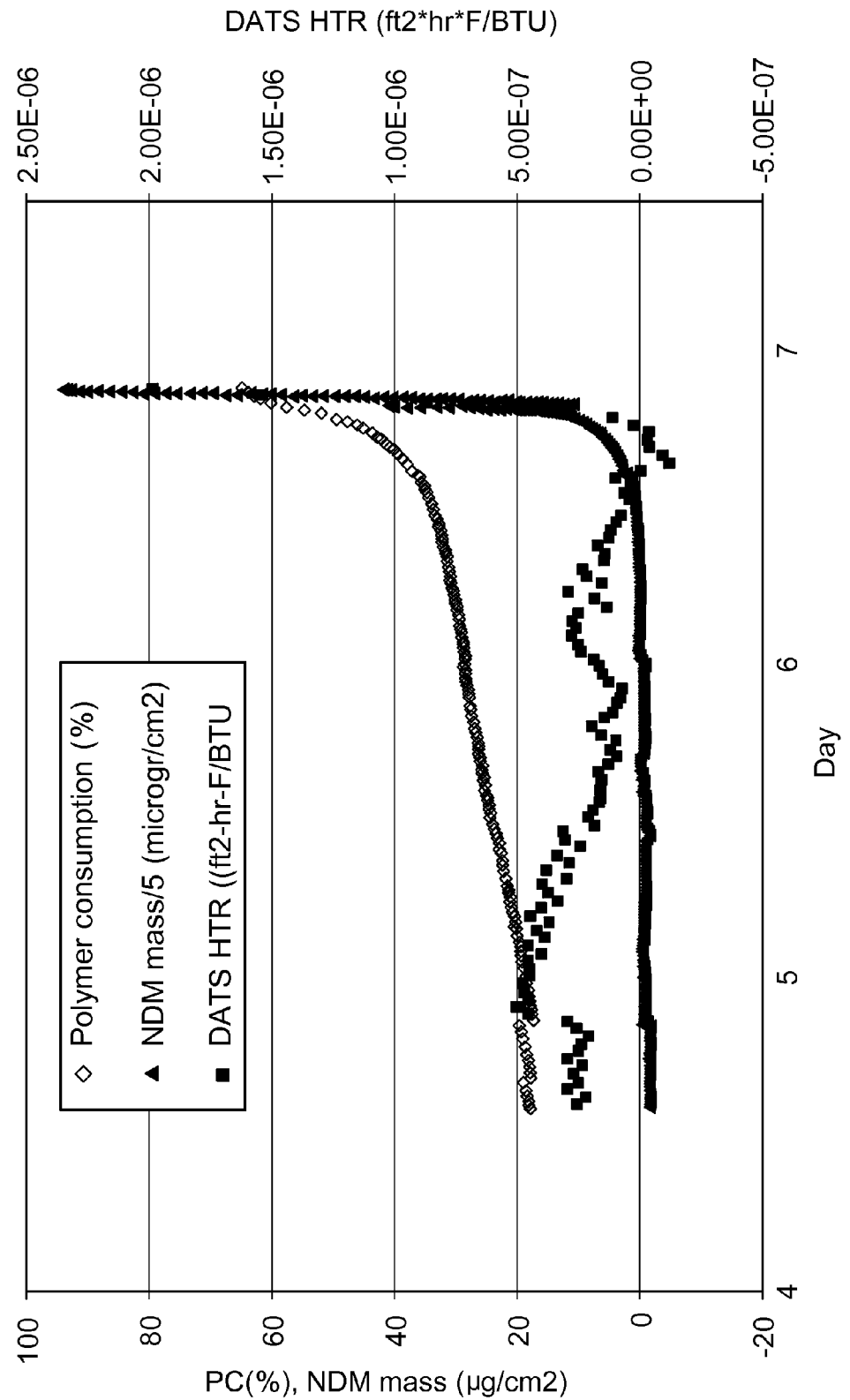
FIG. 12 provides a close-up graphical illustration of the same experiment illustrated in FIGS. 9-11, and additionally compares the fluorometrically-measured polymer consumption, the response of the piezoelectric microbalance sensor, and the response of a DATS HTR device.

Turning to FIG. 12, the graph of FIG. 12 provides a close-up illustration of the same experiment illustrated in FIGS. 9-11, and additionally compares the fluorometrically-measured polymer consumption, the response of the piezoelectric microbalance sensor, and the response of a DATS HTR device.

The DATS HTR device, available from Bridger Scientific, Sagamore Beach, Mass., correlates scaling deposition by quantifying a change in heat transfer resistance ("HTR") as scaling deposition occurs within a heated tubular chamber. The heated tubular chamber allows for sample flow, and the heat load, flow rate, and surface temperature are adjustable. As deposits accumulate in the heated tubular chamber, the chamber becomes more insulated, which results in a HTR that can be correlated with scaling deposition thickness.

Figure 13:
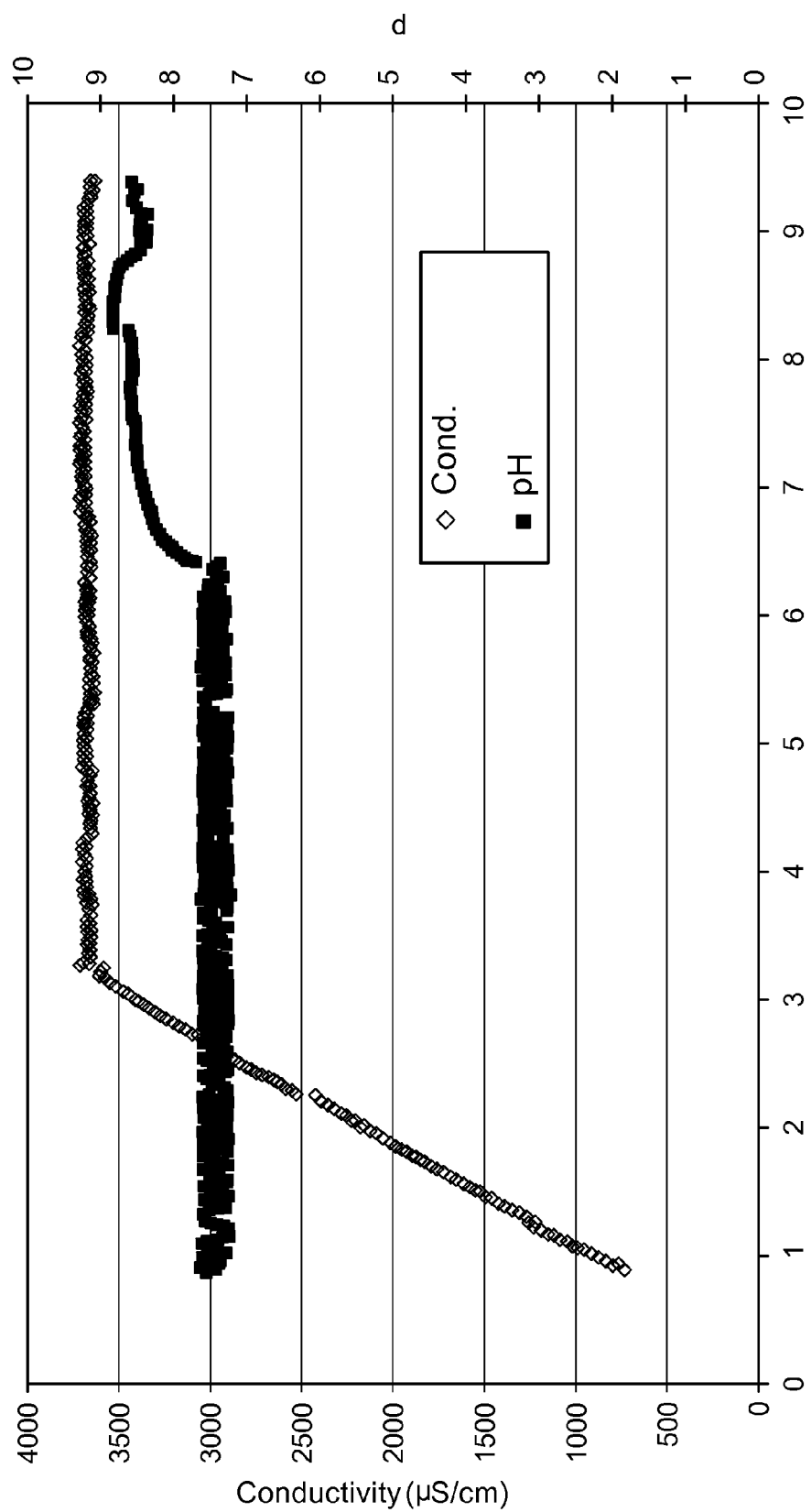
FIG. 13 graphically illustrates the response of a conductivity meter to a loss of pH control.

Turning to FIG. 13, the graph of FIG. 13 illustrates the response of a conductivity meter to a loss of pH control. Acidic buffering of the cooling water was stopped around Day 7, which caused an increase in pH. The conductivity meter did not respond to the elevated pH during the three days subsequent the disruption in acidic buffering.

Figure 14:
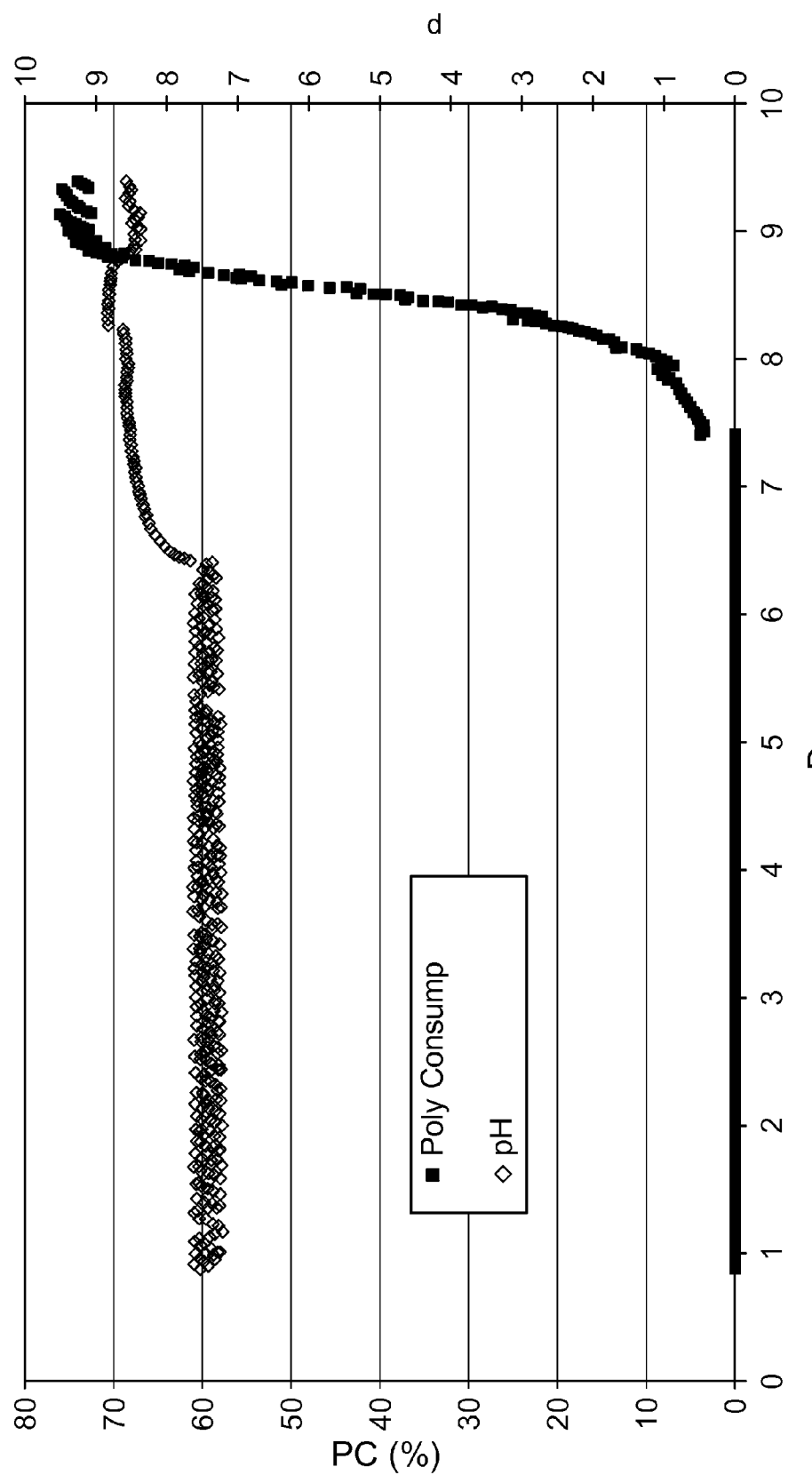
FIG. 14 graphically illustrates the fluorometric response to polymer consumption after the acidic buffering disruption illustrated in FIG. 13.

Turning to FIG. 14, the graph of FIG. 14 illustrates the fluorometric response to polymer consumption after the acidic buffering disruption illustrated in FIG. 13. The fluorometric response occurred within 24 hours of the acidic buffering being stopped.

Figure 15:
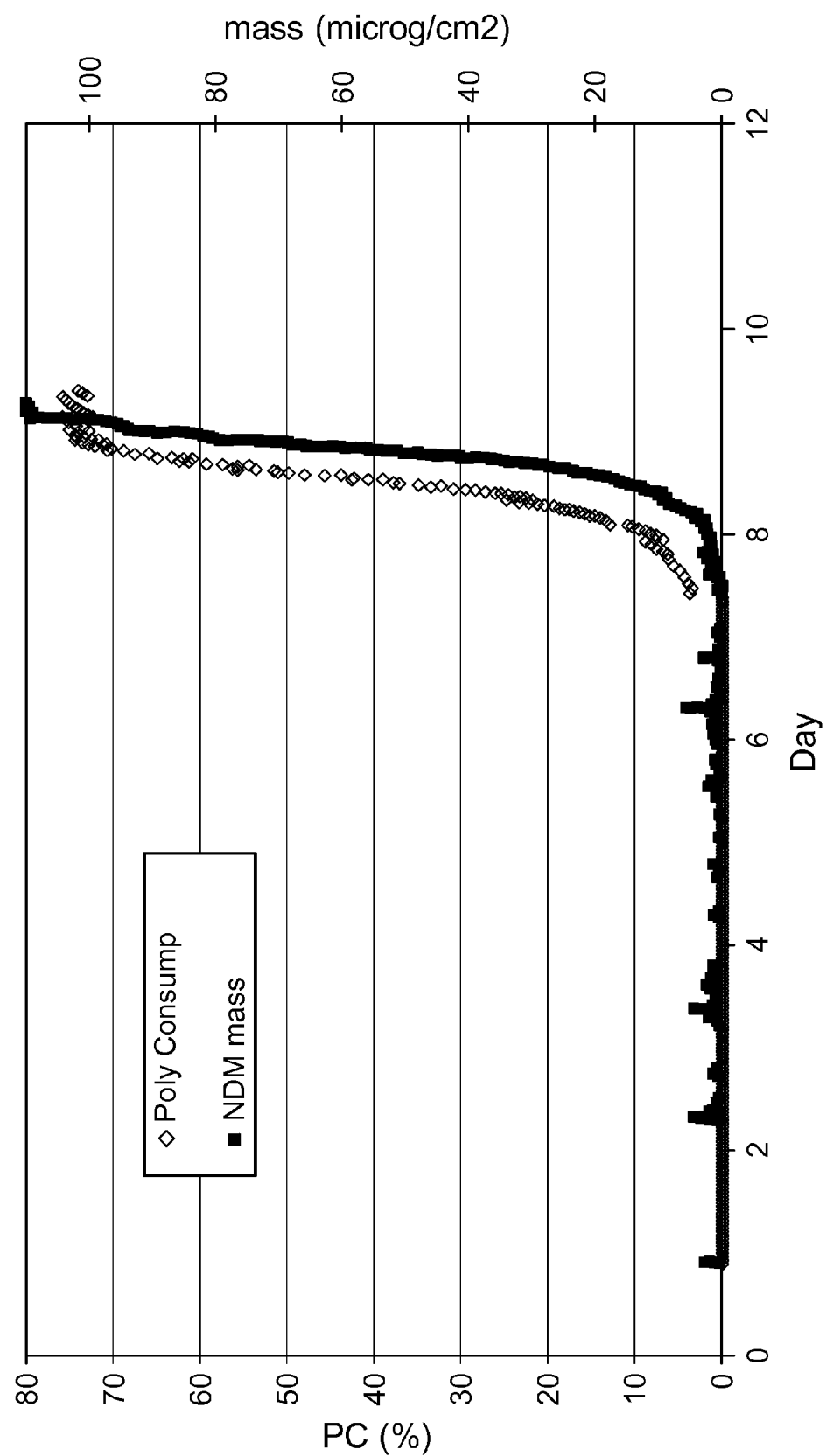
FIG. 15 graphically illustrates the piezoelectric microbalance sensor response for the same experiment illustrated in FIGS. 13 and 14.

Turning to FIG. 15, the graph of FIG. 15 illustrates the piezoelectric microbalance sensor response for the same experiment illustrated in FIGS. 13 and 14. Notice the slightly delayed response as compared to the fluorometric response, which is illustrated as "Poly Consump (%)," and "NDM mass" representing the response of the piezoelectric microbalance sensor.

Figure 16:
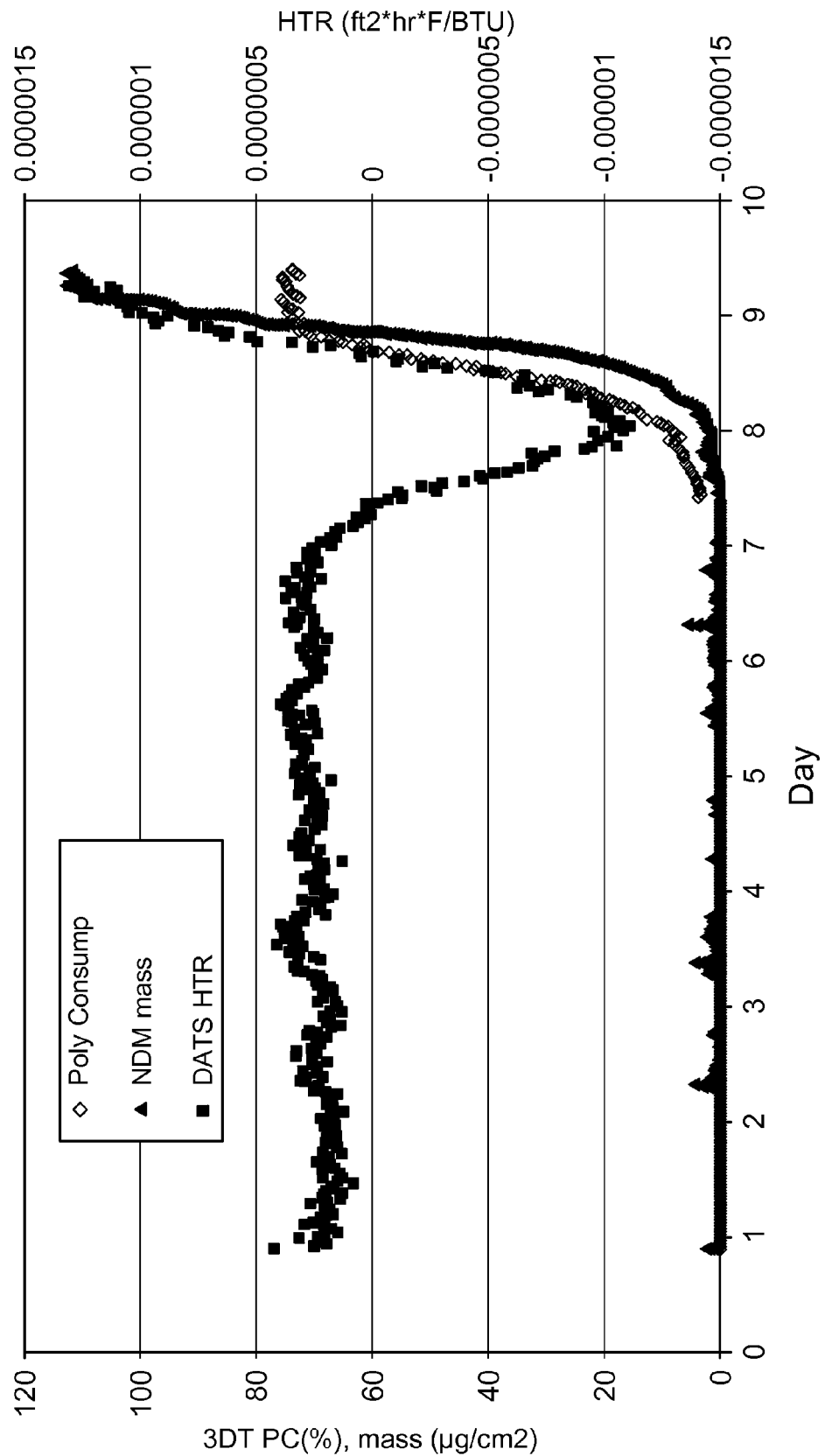
FIG. 16 compares the fluorometric response and the piezoelectric response to the response of a DATS HTR device for the same experiment illustrated in FIGS. 13-15.

Turning to FIG. 16, the graph of FIG. 16 compares the fluorometric response and the piezoelectric response to the response of a DATS HTR device for the same experiment illustrated in FIGS. 13-15.

Overall, the experiments illustrate that the piezoelectric microbalance sensor can be used to detect scaling and to provide input to control scale-inhibiting treatment of an aqueous cooling system. Preferably, the utilization of fluorometric consumption monitoring and dosage control, along with monitoring process response from a piezoelectric microbalance sensor, provides additional benefit to the aqueous cooling system operator, thereby providing added reliability in cooling water treatment control.

Any patents referred to herein, are hereby incorporated herein by reference, whether or not specifically done so within the text of this disclosure.

To the extent that the terms "include," "includes," or "including" are used in the specification or the claims, they are intended to be inclusive in a manner similar to the term "comprising" as that term is interpreted when employed as a transitional word in a claim. Furthermore, to the extent that the term "or" is employed (e.g., A or B), it is intended to mean "A or B or both A and B." When the applicants intend to indicate "only A or B but not both," then the term "only A or B but not both" will be employed. Thus, use of the term "or" herein is the inclusive, and not the exclusive use. See Bryan A. Garner, A Dictionary of Modern Legal Usage 624 (2d ed. 1995). Also, to the extent that the terms "in" or "into" are used in the specification or the claims, it is intended to additionally mean "on" or "onto." Furthermore, to the extent that the term "connect" is used in the specification or the claims, it is intended to mean not only "directly connected to," but also "indirectly connected to" such as connected through another component or components. In the present disclosure, the words "a" or "an" are to be taken to include both the singular and the plural. Conversely, any reference to plural items shall, where appropriate, include the singular.

All ranges and parameters disclosed herein are understood to encompass any and all sub-ranges assumed and subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more (e.g., 1 to 6.1), and ending with a maximum value of 10 or less (e.g., 2.3 to 9.4, 3 to 8, 4 to 7), and finally to each number 1, 2, 3, 4, 5, 6, 7, 8, 9, and 10 contained within the range.

The general inventive concepts have been illustrated, at least in part, by describing various exemplary embodiments thereof. While these exemplary embodiments have been described in considerable detail, it is not the Applicants' intent to restrict or in any way limit the scope of the appended claims to such detail. Furthermore, the various inventive concepts may be utilized in combination with one another (e.g., the first, second, and third exemplary embodiments may be utilized in combination with each other). Additionally, any particular element recited as relating to a particularly disclosed embodiment should be interpreted as available for use with all disclosed embodiments, unless incorporation of the particular element would be contradictory to the express terms of the embodiment. Additional advantages and modifications will be readily apparent to those skilled in the art. Therefore, the disclosure, in its broader aspects, is not limited to the specific details presented therein, the representative apparatus, or the illustrative examples shown and described. Accordingly, departures may be made from such details without departing from the spirit or scope of the general inventive concepts.

The invention claimed is:

1. An automated method of monitoring a process upset and recovery of an aqueous cooling system, the automated method comprising:
   providing an aqueous cooling system comprising cooling water;
   providing a fluorometer;
   providing a piezoelectric microbalance sensor capable of self-cleaning;
   providing a central control system;
   operably connecting the fluorometer and the piezoelectric microbalance sensor to the aqueous cooling system and the central control system;
   dosing into the cooling water at a dosage rate at least one water-soluble, scale-inhibiting chemical selected from the group consisting of: a naturally fluorescing treatment chemical, a fluorescently tagged treatment chemical, a treatment chemical that has been fluorescently traced, and combinations thereof, thereby resulting in a concentration of the at least one water-soluble, scale-inhibiting chemical within the cooling water;
   fluorometrically measuring the concentration of at least one of the at least one water-soluble, scale-inhibiting chemical in the cooling water with the fluorometer;
   utilizing the piezoelectric microbalance sensor to measure a scaling rate of the cooling water;
   adjusting at least one process variable of the aqueous cooling system in response to at least one of the fluorometric measurement and the measured scaling rate;
   wherein the at least one process variable is selected from the group consisting of the dosage rate of at least one water-soluble, scale-inhibiting chemical; a cooling water circulation rate; a valve opening; a flow rate; a volume; a liquid level; pH of the cooling water; blowdown cycle frequency; triggering of an alarm; triggering of a warning; and combinations thereof.

2. The automated method of claim 1, wherein the piezoelectric microbalance sensor comprises:
   i. a piezoelectric material having a process side suitable for contacting a cooling water stream and a non-process side, at least a portion of the process side engaging a process side electrode, and at least a portion of the non-process side engaging a non-process side electrode;
   ii. a heater capable of heating the piezoelectric material from the non-process side and thereby enabling temperature control of the piezoelectric material;
   iii. a counter-electrode having a first surface suitable for contacting the cooling water stream and facing the process side of the piezoelectric material, and a second opposing surface, the counter-electrode positioned within the piezoelectric microbalance sensor so as to allow flow of at least a portion of the cooling water stream between the process side of the piezoelectric material and the first surface of the counter-electrode, wherein the counter-electrode is constructed of an electrically-conducting, corrosion-resistant material; and iv. a pressure-compensating spacer operably contacting the second opposing surface of the counter-electrode, the pressure-compensating spacer capable of compressing and expanding in response to variations in pressure created by the cooling water stream passing through the piezoelectric microbalance sensor.

3. The automated method of claim 2, wherein the piezoelectric material is a quartz crystal.

4. The automated method of claim 3, wherein a resistance temperature detector trace is in operable contact with at least a portion of the non-process side of the piezoelectric material thereby allowing for direct temperature measurement of the piezoelectric material.

5. The automated method of claim 4, wherein the resistance temperature detector trace consists of platinum.

6. The automated method of claim 5, wherein the resistance temperature detector trace has a square wave serpentine pattern surrounding at least a portion of the non-process side electrode.

7. The automated method of claim 6, wherein the pressure-compensating spacer is selected from the group consisting of at least one bellows, at least one diaphragm, at least one O-ring, at least one gasket, and combinations thereof.

8. An automated method for monitoring dosage and process response of an aqueous cooling system, the automated method comprising:
providing an aqueous cooling system comprising cooling water;
providing a fluorometer;
providing a piezoelectric microbalance sensor capable of self-cleaning;
providing a central control system;
operably connecting the fluorometer and the piezoelectric microbalance sensor to the aqueous cooling system and the central control system;
dosing into the cooling water at least one water-soluble, scale-inhibiting chemical selected from the group consisting of: a naturally fluorescing treatment chemical, a fluorescently tagged treatment chemical, a treatment chemical that has been fluorescently traced, and combinations thereof, thereby resulting in a concentration of the at least one water-soluble, scale-inhibiting chemical within the cooling water;
fluorometrically measuring the concentration of at least one of the at least one water-soluble, scale-inhibiting chemical in the cooling water with the fluorometer;
utilizing the piezoelectric microbalance sensor to measure a scaling rate of the cooling water;
adjusting at least one process variable of the aqueous cooling system in response to at least one of the fluorometrically measured concentration and the measured scaling rate;
wherein the at least one process variable is selected from the group consisting of the dosage rate of at least one water-soluble, scale-inhibiting chemical; a cooling water circulation rate; a valve opening; a flow rate; a volume; a liquid level; pH of the cooling water; blowdown cycle frequency; triggering of an alarm; triggering of a warning; and combinations thereof.

9. The automated method of claim 8, wherein the at least one water-soluble, scale-inhibiting chemical is a fluorescently traced or tagged treatment chemical selected from the group consisting of: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts, dimethylamino ethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethacrylate, polyethylene glycol dimethacrylate, glycidyl methacrylate, acrylamidomethylpropane sulfonic acid and the sodium salt thereof, vinyl alcohol, vinyl acetate, N-vinylpyrrolidone, and combinations thereof.

10. The automated method of claim 8, wherein the central control system is capable of automatically cycling self-cleaning of the piezoelectric microbalance sensor.

11. The automated method of claim 10, wherein the piezoelectric microbalance sensor is self-cleaned in cycles at regular time intervals.

12. The automated method of claim 10, wherein the piezoelectric microbalance sensor is self-cleaned in response to the measured scaling rate.

13. An automated method for diagnosing process response to changes in feed water chemistry of a fluorometrically monitored and treated aqueous cooling system, the automated method comprising:
providing an aqueous cooling system comprising cooling water;
providing a fluorometer;
providing a piezoelectric microbalance sensor capable of self-cleaning;
providing a central control system;
operably connecting the fluorometer and the piezoelectric microbalance sensor to the aqueous cooling system and the central control system;
dosing into the cooling water at least one water-soluble, scale-inhibiting chemical selected from the group consisting of: a naturally fluorescing treatment chemical, a fluorescently tagged treatment chemical, a treatment chemical that has been fluorescently traced, and combinations thereof, thereby resulting in a concentration of the at least one water-soluble, scale-inhibiting chemical within the cooling water;
fluorometrically measuring the concentration of at least one of the at least one water-soluble, scale-inhibiting chemical in the cooling water with the fluorometer;
utilizing the piezoelectric microbalance sensor to measure a scaling rate of the cooling water;
adjusting at least one process variable of the aqueous cooling system in response to at least one of the fluorometric measurement and the measured scaling rate;
wherein the at least one process variable is selected from the group consisting of the dosage rate of at least one water-soluble, scale-inhibiting chemical; a cooling water circulation rate; a valve opening; a flow rate; a volume; a liquid level; pH of the cooling water; blowdown cycle frequency; triggering of an alarm; triggering of a warning; and combinations thereof.

14. The automated method of claim 13, wherein the piezoelectric microbalance sensor is self-cleaned in cycles at regular time intervals.

15. The automated method of claim 13, wherein the piezoelectric microbalance sensor is self-cleaned in response to the measured scaling rate.

* * * * *